US012702718B2

(12) United States Patent
Cabral et al.

(10) Patent No.: US 12,702,718 B2
(45) Date of Patent: Aug. 11, 2026

(54) PROTEIN-ENCLOSING POLYMERIC MICELLE

(71) Applicant: THE UNIVERSITY OF TOKYO, Tokyo (JP)

(72) Inventors: Horacio Cabral, Tokyo (JP); Anqi Tao, Tokyo (JP); Kazunori Igarashi, Tokyo (JP); Takuya Miyazaki, Tokyo (JP); George Lo Huang, Tokyo (JP); Pengwen Chen, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 1119 days.

(21) Appl. No.: 17/623,144

(22) PCT Filed: Jun. 25, 2020

(86) PCT No.: PCT/JP2020/025086
§ 371 (c)(1),
(2) Date: Dec. 27, 2021

(87) PCT Pub. No.: WO2020/262550
PCT Pub. Date: Dec. 30, 2020

(65) Prior Publication Data

US 2022/0249689 A1 Aug. 11, 2022

Related U.S. Application Data

(60) Provisional application No. 62/868,040, filed on Jun. 28, 2019.

(51) Int. Cl.

| | |
|---|---|
| ***A61K 47/69*** | (2017.01) |
| ***A61K 38/20*** | (2006.01) |
| ***A61K 38/42*** | (2006.01) |
| ***A61K 47/54*** | (2017.01) |
| ***A61K 47/60*** | (2017.01) |

(52) U.S. Cl.
CPC ........ *A61K 47/6907* (2017.08); *A61K 38/208* (2013.01); *A61K 38/42* (2013.01); *A61K 47/545* (2017.08); *A61K 47/60* (2017.08)

(58) Field of Classification Search
CPC .... A61K 47/6907; A61K 47/60; C08G 69/10; C08G 81/00; C08G 69/40
See application file for complete search history.

(56) References Cited

U.S. PATENT DOCUMENTS

| | | | |
|---|---|---|---|
| 6,797,704 | B2 | 9/2004 | Leong et al. |
| 6,919,091 | B2 | 7/2005 | Trubetskoy et al. |
| 7,393,478 | B2 | 7/2008 | Boulikas |
| 8,211,468 | B2 | 7/2012 | Rozema et al. |
| 8,541,548 | B2 | 9/2013 | Rozema |
| 10,059,681 | B2 | 8/2018 | Blokhin et al. |
| 11,839,624 | B2 | 12/2023 | Ryu et al. |
| 11,873,327 | B2 | 1/2024 | Mishra et al. |
| 2001/0000510 | A1 | 4/2001 | Sakurai et al. |
| 2002/0082198 | A1 | 6/2002 | Sakurai et al. |
| 2003/0147958 | A1 | 8/2003 | Ahn et al. |
| 2004/0162235 | A1 | 8/2004 | Trubetskoy et al. |
| 2005/0059577 | A1 | 3/2005 | Ross |
| 2010/0291065 | A1 | 11/2010 | Kabanov et al. |
| 2011/0052917 | A1 | 3/2011 | Kataoka et al. |
| 2012/0046453 | A1 | 2/2012 | Kataoka et al. |
| 2013/0109743 | A1 | 5/2013 | Kataoka et al. |
| 2018/0085395 | A1 | 3/2018 | Nagasaki et al. |
| 2019/0262269 | A1 | 8/2019 | Kurihara et al. |
| 2021/0238347 | A1 | 8/2021 | Lee et al. |
| 2021/0330747 | A1 | 10/2021 | Fischer et al. |
| 2022/0195071 | A1 | 6/2022 | Jones |
| 2022/0249689 | A1 | 8/2022 | Cabral et al. |
| 2023/0165974 | A1 | 6/2023 | Christie et al. |
| 2024/0252696 | A1 | 8/2024 | Smith et al. |
| 2024/0382440 | A1 | 11/2024 | Zambaux |
| 2025/0177545 | A1 | 6/2025 | Cabral et al. |

FOREIGN PATENT DOCUMENTS

| | | |
|---|---|---|
| CN | 101970541 A | 2/2011 |
| CN | 107530279 A | 1/2018 |
| CN | 109842024 A | 4/2019 |

(Continued)

OTHER PUBLICATIONS

Extended European Search Report for European Application No. 20831481.5, dated May 3, 2023.
Heffernan et al., "Disulfide-Crosslinked Polyion Micelles for Delivery of Protein Therapeutics", Annals of Biomedical Engineering, vol. 37, No. 10, Oct. 2009, pp. 1993-2002.
European Communication pursuant to Article 94(3) EPC for European Application No. 20 831 481.5, dated Mar. 13, 2024.
Chen et al., "Polyion Complex Micelles for Protein Delivery," Australian Journal of Chemistry, vol. 71, 2018, pp. 768-780.
Indian Office Action and Search Report for Indian Application No. 202217004241, dated Dec. 15, 2023, with English translation.
Israelian Office Action for Israelian Application No. 289188, dated Dec. 6, 2023.

(Continued)

*Primary Examiner* — Gyan Chandra
(74) *Attorney, Agent, or Firm* — Birch, Stewart, Kolasch & Birch, LLP

(57) ABSTRACT

The present invention provides a polymeric complex comprising a protein and a block copolymer represented by the following formula (1).

(1)

7 Claims, 19 Drawing Sheets
(5 of 19 Drawing Sheet(s) Filed in Color)

(56) References Cited

FOREIGN PATENT DOCUMENTS

| | | | |
|---|---|---|---|
| CN | 116270541 | A | 6/2023 |
| EP | 3 992 229 | A1 | 5/2022 |
| EP | 4 464 336 | A1 | 11/2024 |
| JP | 8-188541 | A | 7/1996 |
| JP | 2005-529931 | A | 10/2005 |
| JP | 2023-102362 | A | 7/2023 |
| RU | 2 526 904 | C2 | 8/2014 |
| WO | WO 97/41831 | A1 | 11/1997 |
| WO | WO 01/93836 | A2 | 12/2001 |
| WO | WO 03/100081 | A2 | 12/2003 |
| WO | WO 2008/104994 | A2 | 9/2008 |
| WO | WO 2008/141155 | A1 | 11/2008 |
| WO | WO 2017/078883 | A1 | 5/2017 |
| WO | WO 2020/262550 | A1 | 12/2020 |
| WO | WO 2021/214658 | A1 | 10/2021 |
| WO | WO 2022/066635 | A1 | 3/2022 |
| WO | WO 2022/212362 | A1 | 10/2022 |
| WO | WO 2023/116702 | A1 | 6/2023 |
| WO | WO 2023/136364 | A1 | 7/2023 |
| WO | WO 2023/238961 | A1 | 12/2023 |
| WO | WO 2024/113423 | A1 | 6/2024 |
| WO | WO 2024/113429 | A1 | 6/2024 |
| WO | WO 2024/190928 | A1 | 9/2024 |
| WO | WO 2024/190929 | A1 | 9/2024 |

OTHER PUBLICATIONS

Russian Office Action and Search Report for Russian Application No. 2022101607, dated Nov. 17, 2023, with English translation.

Singaporean Office Action for Singaporean Application No. 11202114177X, dated Sep. 19, 2023.

Chinese Office Action and Search Report for Chinese Application No. 202080047059.X, dated Jan. 5, 2023, with an English translation.

Abuchowski et al., "Effect of Covalent Attachment of Polyethylene Glycol on Immunogenicity and Circulating Life of Bovine Liver Catalase," The Journal of Biological Chemistry, vol. 252, No. 11, 1977, pp. 3582-3586.

Alconcel et al., "FDA-approved poly(ethylene glycol)-protein conjugate drugs," Polymer Chemistry, vol. 2, 2011, pp. 1442-1448.

Arvinte et al., "Aggregation of biopharmaceuticals in human plasma and human serum," mAbs, vol. 5, No. 3, 2013, pp. 491-500.

Butler et al., "The Use of Maleic Anhydride for the Reversible Blocking of Amino Groups in Polypeptide Chains," Biochemical Journal, vol. 112, 1969, pp. 679-689.

Cabral et al., "Block Copolymer Micelles in Nanomedicine Applications," Chemical Reviews, vol. 118, 2018, pp. 6844-6892.

Canfield, "The Amino Acid Sequence of Egg White Lysozyme," The Journal of Biological Chemistry, vol. 238, No. 8, 1963, pp. 2698-2707.

Chen et al., "Correlation between polymer architecture and polyion complex micelle stability with proteins in spheroid cancer models as seen by light-sheet microscopy," Polymer Chemistry, vol. 10, 2019, pp. 1221-1230.

Darbre et al., "Comparison of the Myoglobin of the Zebra (*Equus burchelli*) with that of the Horse (*Equus caballus*)," Biochimica et Biophysica Acta, vol. 393, 1975, pp. 201-204.

Esquerra et al., "Spectroscopic Evidence for Nanosecond Protein Relaxation after Photodissociation of Myoglobin-CO," Biochemistry, vol. 37, 1998, pp. 17527-17536.

Gerweck et al., "Cellular pH Gradient in Tumor versus Normal Tissue: Potential Exploitation for the Treatment of Cancer," Cancer Research, vol. 56, 1996, pp. 1194-1198.

Harada-Shiba et al., "*Polyion complex micelles as vectors in gene therapy—pharmacokinetics and in vivo gene transfer*," Gene Therapy, vol. 9, 2002, pp. 407-414.

Helmlinger et al., "Interstitial pH and pO2 gradients in solid tumors in vivo: High-resolution measurements reveal a lack of correlation," Nature Medicine, vol. 3, No. 2, 1997, pp. 177-182.

Hirayama et al., "Rapid Confirmation and Revision of the Primary Structure of Bovine Serum Albumin by ESIMS and Frit-FAB LC/MS," Biochemical and Biophysical Research Communications, vol. 173, No. 2, 1990, pp. 639-646.

Hsu et al., "The Origin of the Heme Cotton Effects in Myoglobin and Hemoglobin," Journal of the American Chemical Society, vol. 93, No. 14, 1971, pp. 3515-3525.

International Search Report for International Application No. PCT/JP2020/025086, dated Sep. 8, 2020, with an English translation.

Japanese Office Action for Japanese Application No. 2021-527739, dated Mar. 8, 2022, with an English translation.

Kagen et al., "Myoglobin Binding in Human Serum," Clinical Chemistry, vol. 23, No. 10, 1977, pp. 1813-1818.

Kim et al., "Intracellular Delivery of Charge-Converted Monoclonal Antibodies by Combinatorial Design of Block/Homo Polyion Complex Micelles," Biomacromolecules, vol. 17, 2016, pp. 446-453.

Kishimura et al., "Encapsulation of Myoglobin in PEGylated Polyion Complex Vesicles Made from a Pair of Oppositely Charged Block Ionomers: A Physiologically Available Oxygen Carrier," Angewandte Chemie International Edition, vol. 46, 2007, pp. 6085-6088.

Langer et al., "Designing materials for biology and medicine," Nature, vol. 428, 2004, pp. 487-492.

Lee et al., "Charge-Conversional Polyionic Complex Micelles—Efficient Nanocarriers for Protein Delivery into Cytoplasm," Angewandte Chemie International Edition, vol. 48, 2009, pp. 5309-5312.

Lee et al., "Efficient Delivery of Bioactive Antibodies into the Cytoplasm of Living Cells by Charge-Conversional Polyion Complex Micelles," Angewandte Chemie International Edition, vol. 49, 2010, pp. 2552-2555.

Li et al., "Spectroscopic and electrochemical studies of horse myoglobin in dimethyl sulfoxide," Journal of Biological Inorganic Chemistry, vol. 8, 2003, pp. 83-94.

Lu et al., "Stimuli-responsive nanomaterials for therapeutic protein delivery," Journal of Controlled Release, vol. 194, 2014, pp. 1-19.

Maier et al., "Acid-Labile Traceless Click Linker for Protein Transduction," Journal of the American Chemical Society, vol. 134, 2012, pp. 10169-10173.

Matsumoto et al., "Direct and instantaneous observation of intravenously injected substances using intravital confocal micro-videography," Biomedical Optics Express, vol. 1, No. 4, 2010, pp. 1209-1216.

Mura et al., "Stimuli-responsive nanocarriers for drug delivery," Nature Materials, vol. 12, 2013, pp. 991-1003.

Qi et al., "Protein-polymer conjugation—moving beyond PEGylation," Current Opinion in Chemical Biology, vol. 28, 2015, pp. 181-193.

Radola, "Isoelectric focusing in layers of granulated gels: I. Thin-layer isoelectric focusing of proteins," Biochimica et Biophysica Acta, vol. 295, 1973, pp. 412-428.

Romberg et al., "Sheddable Coatings for Long-Circulating Nanoparticles," Pharmaceutical Research, vol. 25, No. 1, 2008, pp. 55-71.

Rozema et al., "Dynamic PolyConjugates for targeted in vivo delivery of siRNA to hepatocytes," PNAS, vol. 104, No. 32, 2007, pp. 12982-12987.

Rozema et al., "Endosomolysis by Masking of a Membrane-Active Agent (EMMA) for Cytoplasmic Release of Macromolecules," Bioconjugate Chemistry, vol. 14, 2003, pp. 51-57.

Russell et al., "Next Generation Protein-Polymer Conjugates," AIChE Journal, vol. 64, No. 9, 2018, pp. 3230-3245.

Shi et al., "Influence of pH and Tonic Strength on the Steric Mass-Action Model Parameters around the Isoelectric Point of Protein," Biotechnology Progress, vol. 21, 2005, pp. 516-523.

Sun et al., "Facile Generation of Tumor-pH-Labile Linkage-Bridged Block Copolymers for Chemotherapeutic Delivery," Angewandte Chemie International Edition, vol. 55, 2016, pp. 1010-1014.

Takemoto et al., "Polyion complex stability and gene silencing efficiency with a siRNA-grafted polymer delivery system," Biomaterials, vol. 31, 2010, pp. 8097-8105.

Tangsangasaksri et al., "siRNA-Loaded Polyion Complex Micelle Decorated with Charge-Conversional Polymer Tuned to Undergo Stepwise Response to Intra-Tumoral and Intra-Endosomal pHs for Exerting Enhanced RNAI Efficacy," Biomacromolecules, vol. 17, 2016, pp. 246-255.

(56) References Cited

OTHER PUBLICATIONS

Torchilin, "Tumor delivery of macromolecular drugs based on the EPR effect," Advanced Drug Delivery Reviews, vol. 63, 2011, pp. 131-135.
Vanholder et al., "Rhabdomyolysis," Journal of the American Society of Nephrology, vol. 11, 2000, pp. 1553-1561.
Veronese et al., "PEGylation, successful approach to drug delivery," Drug Discovery Today, vol. 10, No. 21, 2005, pp. 1451-1458.
Veronese et al., "The Impact of PEGylation on Biological Therapies," Biodrugs, vol. 22, No. 5, 2008, pp. 315-329.
Wang et al., "Effects of Salt on Polyelectrolyte-Micelle Coacervation," Macromolecules, vol. 32, 1999, pp. 7128-7134.
Wetter et al., "Immunological studies on egg white proteins. IV. Immunochemical and physical studies of lysozyme," Journal of Biological Chemistry, vol. 192, 1951, pp. 237-242.
Xu et al., "pH-triggered charge-reversal and redox-sensitive drug-release polymer micelles codeliver doxorubicin and triptolide for prostate tumor therapy," International Journal of Nanomedicine, vol. 13, 2018, pp. 7229-7249.
Yen et al., "Light-Induced Cytosolic Activation of Reduction-Sensitive Camptothecin-Loaded Polymeric Micelles for Spatiotemporally Controlled in Vivo Chemotherapy," ACS Nano, vol. 8, No. 11, 2014, pp. 11591-11602.
European Communication pursuant to Article 94(3) EPC for European Application No. 20 831 481.5, dated Apr. 3, 2025.
Indian Office Action for Indian Application No. 202217004241, dated Dec. 6, 2024, with English translation.
Alix et al., "Superagonist, Full Agonist, Partial Agonist, and Antagonist Actions of Arylguanidines at 5-Hydroxytryptamine-3 (5-HT3) Subunit A Receptors," ACS Chemical Neuroscience, vol. 7, Aug. 17, 2016, pp. 1565-1574.
Au et al., "Delivery of cancer therapeutics to extracellular and intracellular targets: Determinants, barriers, challenges and opportunities," Adv. Drug Deliv. Rev., vol. 97, Feb. 1, 2016, pp. 280-301 (53 pages total).
Carlier et al., "Discovery of Non-Zwitterionic GABAA Receptor Full Agonists and a Superagonist," Bioorganic & Medicinal Chemistry Letters, vol. 12, 2002, pp. 1985-1988.
Casey et al., "Sensors and regulators of intracellular pH," Nature Reviews, Molecular Cell Biology, vol. 11, Jan. 2010, pp. 50-61.
Chen et al., "Nanocarriers escaping from hyperacidified endo/lysosomes in cancer cells allow tumor-targeted intracellular delivery of antibodies to therapeutically inhibit c-MYC," Biomaterials, vol. 288, 121748, 2022, pp. 1-17.
Degors et al., "Carriers Break Barriers in Drug Delivery: Endocytosis and Endosomal Escape of Gene Delivery Vectors," Accounts of Chemical Research, vol. 52, 2019, pp. 1750-1760.
English translation of the International Search Report for International Application No. PCT/JP2023/022516, dated Aug. 22, 2023.
English translation of the Written Opinion of the International Searching Authority for International Application No. PCT/JP2023/022516, dated Aug. 22, 2023.
Erazo-Oliveras et al., "Improving the Endosomal Escape of Cell-Penetrating Peptides and Their Cargos: Strategies and Challenges," Pharmaceuticals, vol. 5, 2012, pp. 1177-1209.
Galloway et al., "Peptide Super-Agonist Enhances T-Cell Responses to Melanoma," Frontiers in Immunology, vol. 10, Article 319, Mar. 13, 2019, pp. 1-18.
Gilleron et al., "Image-based analysis of lipid nanoparticle-mediated siRNA delivery, intracellular trafficking and endosomal escape," Nature Biotechnology, vol. 31, No. 7, Jul. 2013, pp. 638-646 (12 pages total).
Han et al., "An ionizable lipid toolbox for RNA delivery," Nature Communications, vol. 12, No. 7233, 2021, pp. 1-6.
Han et al., "Effects of hydrophobic core components in amphiphilic PDMAEMA nanoparticles on siRNA delivery," Biomaterials, vol. 48, 2015, pp. 45-55.
Hanahan et al., "Hallmarks of Cancer: The Next Generation," Cell, vol. 144, Mar. 4, 2011, pp. 646-674.
International Search Report (PCT/ISA/210) issued in PCT/JP2023/001601, dated Mar. 7, 2023, with an English translation.
Japanese Office Action for Japanese Application No. 2022-084284, dated Jan. 7, 2025, with English translation.
Jhaveri et al., "Intracellular delivery of nanocarriers and targeting to subcellular organelles," Expert Opinion on Drug Delivery, vol. 13, No. 1, 2015, pp. 49-70.
Jiang et al., "Alkalinization of the Lysosomes Is Correlated with ras Transformation of Murine and Human Fibroblasts," The Journal of Biological Chemistry, vol. 265, No. 9, 1990, pp. 4775-4777.
Jiang et al., "Gel-Liposome-Mediated Co-Delivery of Anticancer Membrane-Associated Proteins and Small-Molecule Drugs for Enhanced Therapeutic Efficacy," Advanced Functional Materials, vol. 24, 2014, pp. 2295-2304.
Kardani et al., "Cell penetrating peptides: the potent multi-cargo intracellular carriers," Expert Opinion on Drug Delivery, vol. 16, No. 11, 2019, pp. 1227-1258.
Ko et al., "Emerging links between endosomal pH and cancer," Cancer Metastasis Rev., vol. 39, No. 2, 2020, pp. 519-534 (25 pages total).
Lee et al., "Charge-Conversion Ternary Polyplex with Endosome Disruption Moiety: A Technique for Efficient and Safe Gene Delivery," Angewandte Chemie, vol. 120, 2008, pp. 5241-5244.
Lee et al., "DNA-inspired nanomaterials for enhanced endosomal escape," Proc. Natl. Acad. Sci. U.S.A., vol. 118, No. 19, e2104511118, 2021, pp. 1-3.
Lucien et al., "Hypoxia-induced mobilization of NHE6 to the plasma membrane triggers endosome hyperacidification and chemoresistance," Nature Communications, vol. 8, No. 15884, Jun. 21, 2017, pp. 1-15.
Mi et al., "Clinical Translation of Self-Assembled Cancer Nanomedicines," Advanced Therapeutics, vol. 4, 2000159, 2021, pp. 1-29.
Nishimura et al., "A display of pH-sensitive fusogenic GALA peptide facilitates endosomal escape from a Bio-nanocapsule via an endocytic uptake pathway," Journal of Nanobiotechnology, vol. 12, No. 11, 2014, pp. 1-6.
Qin et al., "Rational Design of Nanocarriers for Intracellular Protein Delivery," Advanced Materials, vol. 31, 1902791, 2019, pp. 1-32.
Ray et al., "Intracellular delivery of proteins by nanocarriers," Nanomedicine, vol. 12, No. 8, 2017, pp. 941-952.
Sahay et al., "Efficiency of siRNA delivery by lipid nanoparticles is limited by endocytic recycling," Nat. Biotechnol., vol. 31, No. 7, Jul. 2013, pp. 653-658 (14 pages total).
Sahin et al., "mRNA-based therapeutics—developing a new class of drugs," Nat. Rev. Drug Discovery, 2014, vol. 13, pp. 759-780.
Sasaki et al., "An artificial virus-like nano carrier system: enhanced endosomal escape of nanoparticles via synergistic action of pH-sensitive fusogenic peptide derivatives," Anal. Bioanal. Chem., vol. 391, 2008, pp. 2717-2727.
Sato et al., "A pH-sensitive cationic lipid facilitates the delivery of liposomal siRNA and gene silencing activity in vitro and in vivo," Journal of Controlled Release, vol. 163, 2012, pp. 267-276,.
Scaletti et al., "Protein Delivery into Cells using Inorganic Nanoparticle-Protein Supramolecular Assemblies," Chemical Society Reviews, vol. 47, 2018, pp. 1-23.
Schrage et al., "Superagonism at G protein-coupled receptors and beyond," British Journal of Pharmacology, vol. 173, 2016, pp. 3018-3027.
Shi et al., "The EPR effect and beyond: Strategies to improve tumor targeting and cancer nanomedicine treatment efficacy," Theranostics, vol. 10, Issue 17, 2020, pp. 7921-7924.
Smith et al., "The Endosomal Escape of Nanoparticles: Toward More Efficient Cellular Delivery," Bioconjugate Chemistry, vol. 30, 2019, pp. 263-272.
Song et al., "Inspired by nonenveloped viruses escaping from endo-lysosomes: a pH-sensitive polyurethane micelle for effective intracellular trafficking," Nanoscale, vol. 8, 2016, pp. 7711-7722.
Stebbings et al., "Safety of biologics, lessons learnt from TGN1412," Current Opinion in Biotechnology, vol. 20, 2009, pp. 673-677.
Stoeckl et al., "Identification of a structural motif crucial for infectivity of hepatitis B viruses," Proc. Natl. Acad. Sci., vol. 103, No. 17, Apr. 25, 2006, pp. 6730-6734.

(56) References Cited

OTHER PUBLICATIONS

Tao et al., "Polymeric Micelles Loading Proteins through Concurrent Ion Complexation and pH-Cleavable Covalent Bonding for In Vivo Delivery," Macromolecular Bioscience, vol. 20, 1900161, 2020, pp. 1-11.
Tsui et al., "Stability of Endogenous and Added RNA in Blood Speciments, Serum, and Plasma," Clinical Chemistry, 2002, vol. 48, pp. 1647-1653.
Tugues et al., "New insights into IL-12-mediated tumor suppression," Cell Death and Differentiation, vol. 22, 2015, pp. 237-246.
Uchida et al., "Systemic delivery of messenger RNA for the treatment of pancreatic cancer using polyplex nanomicelles with a cholesterol moiety." Biomaterials, 2016, vol. 82, pp. 221-228.
Wang, "pH-Responsive Amphiphilic Carboxylate Polymers: Design and Potential for Endosomal Escape," Frontiers in Chemistry, vol. 9, Article 645297, Mar. 23, 2021, pp. 1-8.
White et al., "Fusion of Enveloped Viruses in Endosomes," Traffic, vol. 17, 2016, pp. 593-614.
Wrangle et al., "ALT-803, an IL-15 superagonist, in combination with nivolumab in patients with metastatic non-small cell lung cancer: a non-randomised, open-label, phase 1b trial," Lancet Oncol., vol. 19, No. 5, May 2018, pp. 694-704 (24 pages total).
Written Opinion of the International Searching Authority (PCT/ISA/237) issued in PCT/JP2023/001601, dated Mar. 7, 2023.
Written Opinion of the International Searching Authority for International Application No. PCT/JP2020/025086, dated Sep. 8, 2020, with an English translation.
Yang et al., "Cell-Penetrating Peptide Induces Leaky Fusion of Liposomes Containing Late Endosome-Specific Anionic Lipid," Biophysical Journal, vol. 99, No. 8, Oct. 2010, pp. 2525-2533.
Yang et al., "Polymeric Micelles with pH-Responsive Cross-Linked Core Enhance In Vivo mRNA Delivery", Pharmaceutics, 2022, vol. 14, total 11 pages.
Yu et al., "Overcoming Endosomal Barrier by Amphotericin B-Loaded Dual pH-Responsive PDMA-b-PDPA mMcelleplexes for siRNA Delivery," ACS Nano., vol. 5, No. 11, Nov. 22, 2011, pp. 9246-9255 (21 pages total).
Australian Office Action for Australian Application No. 2020305308, dated Jun. 24, 2025.
Japanese Decision of Dismissal of Amendment for Japanese Application No. 2022-084284, dated Jul. 8, 2025, with English translation.
Japanese Decision of Refusal for Japanese Application No. 2022-084284, dated Jul. 8, 2025, with English translation.
U.S. Office Action for U.S. Appl. No. 19/079,771, dated Jul. 15, 2025.
Office Action issued Oct. 16, 2025, in Canadian Patent Application No. 3,144,358.
Chen et al., "An IL-12-Based Nanocytokine Safely Potentiates Anticancer Immunity through Spatiotemporal Control of Inflammation to Eradicate Advanced Cold Tumors," Advanced Science, vol. 10, 2205139, 2023, pp. 1-16.
Chen et al., "Nanoenabled IL-15 Superagonist via Conditionally Stabilized Protein-Protein Interactions Eradicates Solid Tumors by Precise Immunomodulation," Journal of American Chemical Society, vol. 146, 2024, pp. 32431-32444.
Guo et al., "IL-15/IL-15Ra Heterodimeric Complex as Cancer Immunotherapy in Murine Breast Cancer Models," Frontiers in Immunology, vol. 11, Article 614667, 2021, pp. 1-12.
International Search Report and Written Opinion of the International Searching Authority for International Application No. PCT/JP2025/080050, dated Jun. 3, 2025.
Japanese Office Action for Japanese Application No. 2022-002782, dated Feb. 10, 2026, with English translation.
U.S. Notice of Allowance for U.S. Appl. No. 19/079,771, dated Feb. 10, 2026.

Micelle
Released IL-12
Native IL-12
**
**
Interferon-gama (pg/mL)
100
80
60
40
20
0
0
0.1
1
10
IL-12 Concentration (ng/mL)
** P<0.01, n=5
24 h

PROTEIN-ENCLOSING POLYMERIC MICELLE

CROSS REFERENCE TO RELATED APPLICATIONS

This application is the National Phase of PCT International Application No. PCT/JP2020/025086, filed on Jun. 25, 2020, which claims priority under 35 U.S.C. 119(e) to U.S. Provisional Application No. 62/868,040, filed on Jun. 28, 2019, all of which are hereby expressly incorporated by reference into the present application.

TECHNICAL FIELD

The present invention relates to a protein-enclosing polymeric micelle which is configured to achieve improved stability in a severe in vivo environment by using a block copolymer. All disclosures of the references cited herein are incorporated herein by reference in their entirety.

BACKGROUND ART

Proteins are physiologically active substances found in everywhere in the body, and therefore have been used in the treatment of various intractable diseases including cancers, autoimmune diseases and metabolic disorders. However, when systemically administered alone, proteins undergo enzymatic degradation and/or renal excretion, and further have immunogenicity, so that the biomedical application of proteins requires the development of delivery carriers. For this purpose, efforts have been made to develop protein-PEG conjugates in which a biocompatible polymer, poly(ethylene glycol) (PEG), is introduced into proteins, whereby the problems[1-4] associated with proteins can be overcome by suppressed interactions with proteases and/or immunocytes and increased size. In actual fact, many protein-PEG conjugates have been approved by the FDA, and their market as protein formulations is worth several billions of dollars[5,6]. However, when proteins are PEGylated, their enzymatic degradation, renal excretion and immunogenicity[7,8] are suppressed, although there arise problems such as protein inactivation caused by irreversible chemical modifications to proteins, and insufficient spatial-temporal regulation of protein functions[6,9]. Thus, efforts have been made to develop delivery carriers which are designed to formulate proteins via reversible chemical bonds, whereby the proteins can be released in a target tissue[10] specific manner while suppressing protein expression in normal tissues.

Stimuli-responsive nanocarriers are designed to detect physiologically active substances in target tissues[4,11], whereby proteins can be released in a target tissue specific manner while retaining their activity. Among such nanocarriers, core-shell type polymeric micelles formed upon autonomous association between block copolymer and protein can induce protein release in response to external stimuli[4] by introducing environmentally responsive sites into the core-forming chain of the block copolymer. External stimuli to which polymeric micelles can respond may be exemplified by pH. For example, many diseases (e.g., cancers or autoimmune diseases) show lower pH values (pH 6.5 to 7.2) than normal tissues (pH 7.4)[12,13].

On the other hand, the inventors of the present invention have previously shown that polyion complex (PIC)-type polymeric micelles can be prepared by addition of a PEG-polycation to a protein whose amino groups have been converted into carboxyl groups by a pH-responsive maleic anhydride derivative[14-16]. Micelles of this type enclose a protein stably within the core at normal tissue pH (pH 7.4), but the pH-responsive maleic anhydride derivative is cleaved at an acidic pH in target tissues (pH 6.5 to 7.2), thereby successfully releasing the protein.

However, for their medical application, it is important to improve their blood retention and thereby enhance their accumulation into target tissues.

SUMMARY OF THE INVENTION

Problem to be Solved by the Invention

Accordingly, for enhancement of the therapeutic effect provided by therapeutic proteins, it is important to develop micelles which allow increased blood retention and efficient protein release under acidic conditions.

Means to Solve the Problem

The present invention aimed at increased stability of micelles and efficient release of a protein under acidic conditions by introducing a pH-responsive maleic anhydride derivative into the core-forming chain of a block copolymer to thereby form reversible covalent bonds with amino groups in the protein. Moreover, the present invention aimed at further stabilization of micelles by PIC formation between amino groups in the core-forming chain of the block copolymer and carboxyl groups in the protein. The object of the present invention is to stabilize the structure of micelles by covalent bonding and PIC formation and thereby enhance their blood retention.

Namely, the present invention is as follows.

[1] A polymeric complex comprising a protein and a block copolymer represented by the following formula (1):

(1)

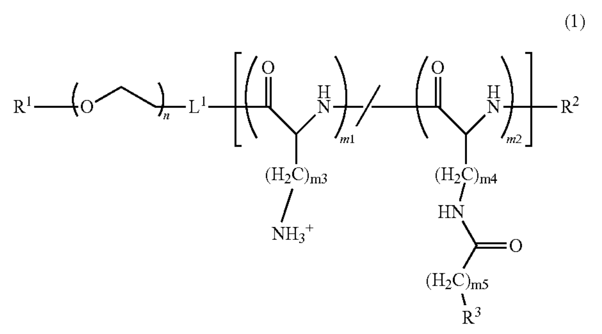

[wherein $R^1$ and $R^2$ each independently represent a hydrogen atom, or an optionally substituted linear or branched alkyl group containing 1 to 12 carbon atoms, or an azide, an amine, maleimide, a ligand or a labeling agent, $R^3$ represents a compound represented by the following formula (I):

(I)

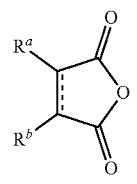

(wherein $R^a$ and $R^b$ each independently represent a hydrogen atom, or an optionally substituted alkyl group, an alkenyl group, a cycloalkyl group, an aryl group, an aralkyl group, an acyl group, a heterocyclic group, a heterocyclic alkyl group, a hydroxy group, an alkoxy group or an aryloxy group. Alternatively, $R^a$ and $R^b$ may be joined with each other to form an aromatic ring or a cycloalkyl ring together with the carbon atoms to which they are attached respectively. The bond between the carbon atoms to which $R^a$ and $R^b$ are attached respectively may be a single bond or a double bond), $L^1$ represents NH, CO, or a group represented by the following formula (11):

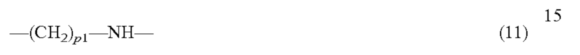

$$—(CH_2)_{p1}—NH— \quad (11)$$

(wherein p1 represents an integer of 1 to 6), or a group represented by the following formula (12):

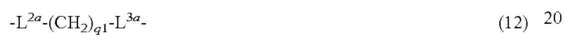

$$-L^{2a}-(CH_2)_{q1}-L^{3a}- \quad (12)$$

(wherein $L^{2a}$ represents OCO, OCONH, NHCO, NHCOO, NHCONH, CONH or COO, $L^{3a}$ represents NH or CO, and q1 represents an integer of 1 to 6), m1 and m2 each independently represent an integer of 0 to 500 (provided that the sum of m1 and m2 represents an integer of 10 to 500), m3, m4 and m5 each independently represent an integer of 1 to 5, and n represents an integer of 0 to 500, and the symbol "/" means that (m1+m2) units of the respective monomer units shown on the left and right sides of this symbol may be in any sequence].

[2] The complex according to [1] above, wherein the compound represented by formula (I) is at least one of compounds represented by the following formulae (Ia) to (Ig).

(Ia)

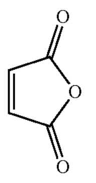

(Ib)

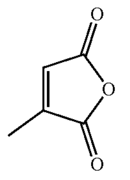

(Ic)

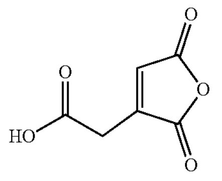

(Id)

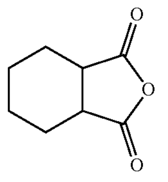

-continued (Ie)

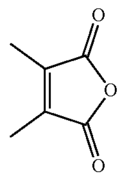

(If)

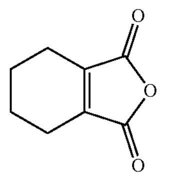

(Ig)

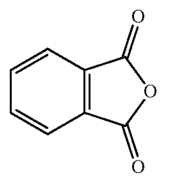

[3] The complex according to [2] above, wherein the compound represented by formula (I) is a compound represented by the following formula (Ia) or (Ib).

(Ia)

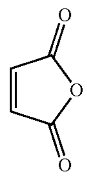

(Ib)

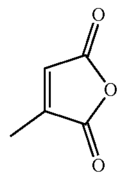

[4] The complex according to [1] above, wherein the block copolymer represented by formula 1 is a block copolymer represented by the following formula (2).

(2)

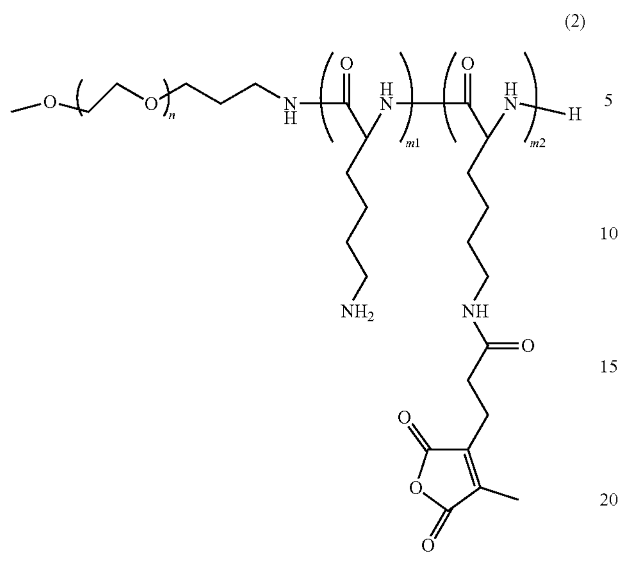

[5] The complex according to [1] above, wherein the protein is covalently bonded to the block copolymer represented by formula 1.

[6] The complex according to [5] above, wherein the covalent bond is cleaved in a pH-dependent manner.

[7] A protein delivery device comprising the polymeric complex according to any one of [1] to [6] above for use in protein delivery to any site selected from a cell surface site, an intracellular site and an extracellular site.

[8] A protein delivery kit comprising a block copolymer represented by the following formula (1) for use in protein delivery to any site selected from a cell surface site, an intracellular site and an extracellular site:

(1)

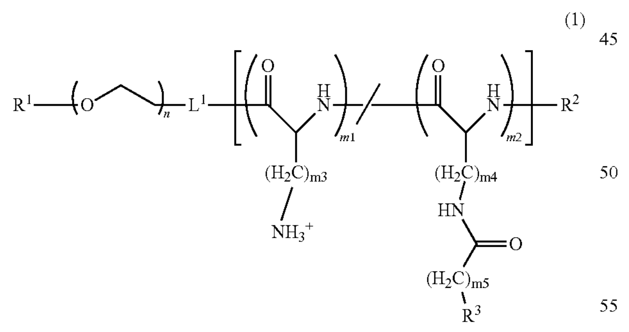

[wherein $R^1$ and $R^2$ each independently represent a hydrogen atom, or an optionally substituted linear or branched alkyl group containing 1 to 12 carbon atoms, or an azide, an amine, maleimide, a ligand or a labeling agent, $R^3$ represents a compound represented by the following formula (I):

(I)

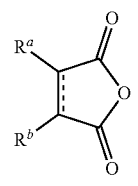

(wherein $R^a$ and $R^b$ each independently represent a hydrogen atom, or an optionally substituted alkyl group, an alkenyl group, a cycloalkyl group, an aryl group, an aralkyl group, an acyl group, a heterocyclic group, a heterocyclic alkyl group, a hydroxy group, an alkoxy group or an aryloxy group. Alternatively, $R^a$ and $R^b$ may be joined with each other to form an aromatic ring or a cycloalkyl ring together with the carbon atoms to which they are attached respectively. The bond between the carbon atoms to which $R^a$ and $R^b$ are attached respectively may be a single bond or a double bond), $L^1$ represents NH, CO, or a group represented by the following formula (11):

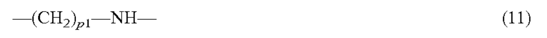

$$-(CH_2)_{p1}-NH- \quad (11)$$

(wherein p1 represents an integer of 1 to 6), or a group represented by the following formula (12):

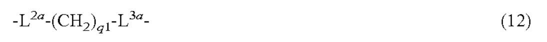

$$-L^{2a}-(CH_2)_{q1}-L^{3a}- \quad (12)$$

(wherein $L^{2a}$ represents OCO, OCONH, NHCO, NHCOO, NHCONH, CONH or COO, $L^{3a}$ represents NH or CO, and q1 represents an integer of 1 to 6), m1 and m2 each independently represent an integer of 0 to 500 (provided that the sum of m1 and m2 represents an integer of 10 to 500), m3, m4 and m5 each independently represent an integer of 1 to 5, and n represents an integer of 0 to 500, and the symbol "/" means that (m1+m2) units of the respective monomer units shown on the left and right sides of this symbol may be in any sequence].

[9] The kit according to [8] above, wherein the compound represented by formula (I) is at least one of compounds represented by the following formulae (Ia) to (Ig).

(Ia)

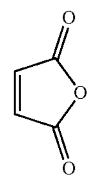

(Ib)

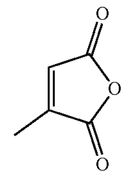

(Ic)

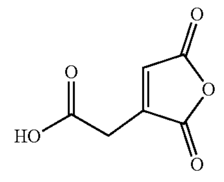

-continued (Id)

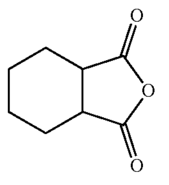

(Ie)

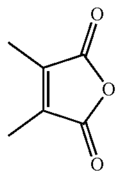

(If)

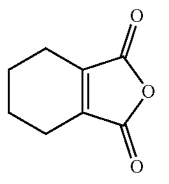

(Ig)

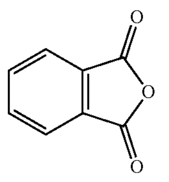

The kit according to [9] above, wherein the compound represented by formula (I) is a compound represented by the following formula (Ia) or (Ib).

(Ia)

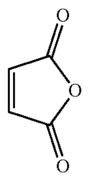

(Ib)

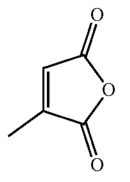

The kit according to [8] above, wherein the block copolymer represented by formula 1 is a block copolymer represented by the following formula (2).

(2)

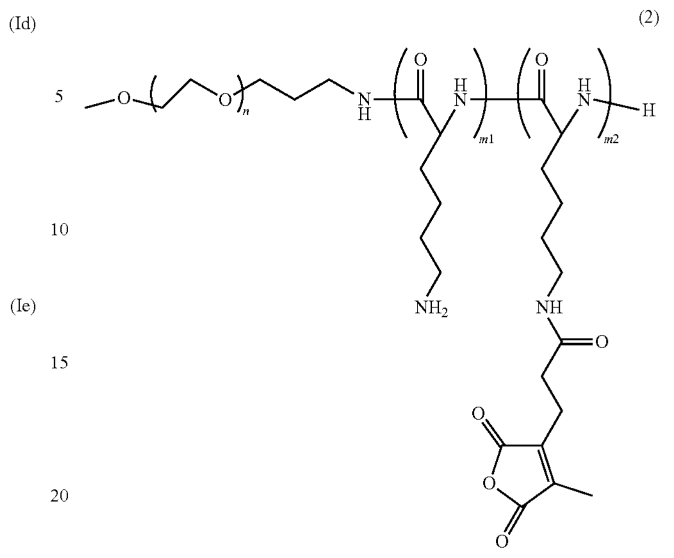

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Although therapeutic proteins are expected to be promising in the treatment of intractable diseases, their systemic administration involves various problems including instability, short half-life, and non-specific immune reactions, etc. Thus, a protein delivery approach using stimuli-responsive nanocarriers may be an effective strategy to enhance protein activity in target tissues in a tissue selective manner. In the present invention, there have been developed polymeric micelles having the ability to form a polyion complex between protein and block copolymer and thereby encapsulate the protein through covalent bonding cleavable under given pH conditions, with the aim of releasing the loaded protein in a pH-dependent manner.

A carboxydimethylmaleic anhydride (CDM)-amide bond is stable at physiological pH (pH 7.4), but is cleaved at pH 6.5, i.e., at pathophysiological pH in tumors and inflammatory tissues. For this reason, CDM was selected as a pH-responsive functional group. In the present invention, a poly(ethylene glycol)-poly(L-lysine) block copolymer with 45% CDM addition was used, whereby different proteins having various molecular weights and isoelectric points were enclosed with an efficiency of 50% or higher. Myoglobin-enclosing micelles (myo/m) were used as a model to confirm micelle stability under physiological conditions, as well as micelle breakdown and functional myoglobin release at pH 6.5. Further, myo/m were found to have an improved blood half-life when compared to myoglobin alone and covalent bond-free micelles associated only by electrostatic interaction. Thus, the above model indicated the usefulness of the system for in vivo delivery of therapeutic proteins.

Figure 1:
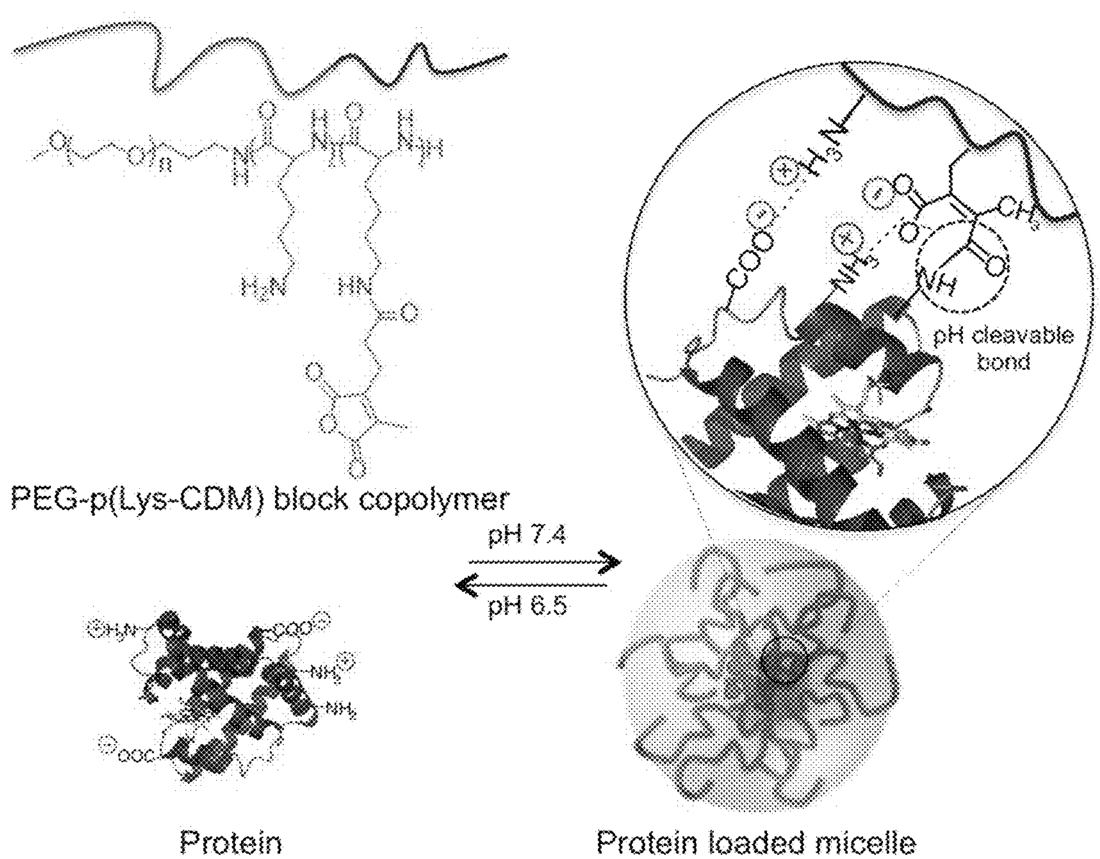
FIG. 1 shows a pH-responsive protein-enclosing micelle based on polyion complex formation and pH-responsive amide bonding.

The CDM-amide bond is unstable at pH 6.5[17-19] and thereby allows release of the conjugated amino compound at pathological pH, so that CDM was selected as a pH-responsive site in the present invention. Thus, the resulting protein-enclosing micelles each form a stable crosslinked core at physiological pH, but are degraded at pH 6.5 into a free block copolymer and an active protein (FIG. 1). In the present invention, these micelles were evaluated for their ability to enclose various proteins. Further, the inventors of the present invention used micelles enclosing myoglobin or IL-12 as a model to evaluate their in vitro stability and protein release at different pHs, as well as their in vivo blood retention after systemic administration.

1. Polymeric Complex of the Present Invention

The polymeric complex of the present invention is a protein-enclosing polymeric micellar complex (polyion complex: PIC), which comprises a particular type of cationic polymer (e.g., block copolymer, graft copolymer) and a protein (the details of this protein will be described later).

(1) Cationic Polymer

A particular type of cationic polymer, which is a member constituting the PIC of the present invention, is a cationic polymer at least partially having a polycation moiety. Such a cationic polymer may be, for example, a block copolymer or graft polymer having a polyethylene glycol (PEG) moiety and a polycation moiety, without being limited thereto. Depending on the intended use of the PIC of the present invention, a preferred embodiment may be selected as appropriate.

The above PEG and polycation have no limitation on their structure (e.g., their degree of polymerization), and those of any structure may be selected. Above all, preferred as a polycation is a polypeptide having cationic groups in its side chains. As used herein, the term "cationic group" is intended to mean not only a group which is already cationic by being coordinated with hydrogen ions, but also a group which will be cationic when coordinated with hydrogen ions. Such cationic groups include all of the known ones. A polypeptide having cationic groups in its side chains is intended to include those composed of known amino acids having a basic side chain (e.g., lysine, arginine, histidine) linked via peptide bonds, as well as those composed of various amino acids linked via peptide bonds, whose side chain (e.g., the side chain of aspartic acid or glutamic acid) is substituted to have a cationic group.

More specifically, the above particular type of cationic polymer may preferably be exemplified by a block copolymer represented by the following general formula (1).

(1)

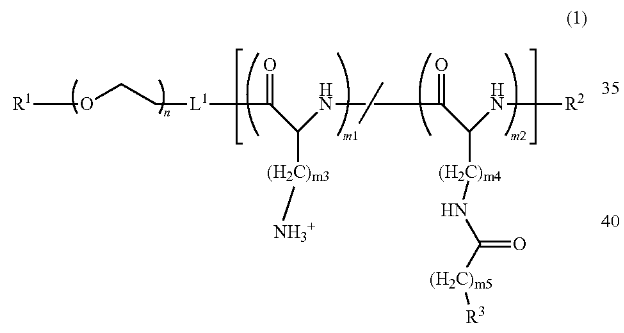

In the structural formula shown in general formula (1), the block moiety whose number of repeating units (degree of polymerization) is n corresponds to the PEG moiety, while the block moiety composed collectively of submoieties whose number of repeating units is m1 and m2, respectively (i.e., the moiety shown in brackets [ ] in general formula (1)) corresponds to the polycation moiety. Moreover, the symbol "/" appearing in the structural formula of the polycation moiety is intended to mean that the respective monomer units shown on the left and right sides of this symbol may be in any sequence. For example, when a block moiety composed of monomer units A and B is represented by [-(A)a-/-(B)b-], the symbol "/" means that a units of A and b units of B, i.e., (a+b) units in total of the respective monomer units may be linked at random in any sequence (provided that all the monomer units A and B are linked in a linear fashion).

In general formula (1), $R^1$ and $R^2$ each independently represent a hydrogen atom, or an optionally substituted linear or branched alkyl group containing 1 to 12 carbon atoms, or a functional group such as an azide, an amine, maleimide, a ligand or a labeling agent.

Examples of the above linear or branched alkyl group containing 1 to 12 carbon atoms include a methyl group, an ethyl group, a n-propyl group, an isopropyl group, a n-butyl group, a sec-butyl group, a tert-butyl group, a n-pentyl group, a n-hexyl group, a decyl group and an undecyl group, etc. Moreover, examples of substituents on the above alkyl group include an acetal-protected formyl group, a cyano group, a formyl group, a carboxyl group, an amino group, an alkoxycarbonyl group containing 1 to 6 carbon atoms, an acylamido group containing 2 to 7 carbon atoms, a siloxy group, a silylamino group, and a trialkylsiloxy group (each alkylsiloxy group independently contains 1 to 6 carbon atoms), etc.

A ligand molecule refers to a compound used with the aim of targeting a certain biomolecule, and examples include an antibody, an aptamer, a protein, an amino acid, a low molecular compound, a monomer of a biological macromolecule and so on. Examples of a labeling agent include, but are not limited to, fluorescent labeling agents such as a rare earth fluorescent labeling agent, coumarin, dimethylaminosulfonyl benzoxadiazole (DBD), dansyl, nitrobenzoxadiazole (NBD), pyrene, fluorescein, a fluorescent protein and so on.

When the above substituent is an acetal-protected formyl group, this substituent can be converted into another substituent, i.e., a formyl group (or an aldehyde group; —CHO) upon hydrolysis under acidic mild conditions. Moreover, when the above substituent (particularly on $R^1$) is a formyl group or is a carboxyl group or an amino group, for example, an antibody or a fragment thereof or other functional or targeting proteins may be linked via these groups.

In general formula (1), $R^3$ represents a compound represented by the following general formula (I).

(I)

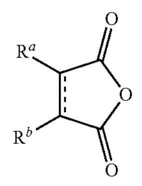

In the above formula (I), $R^a$ and $R^b$ each independently represent a hydrogen atom, or an optionally substituted alkyl group, an alkenyl group, a cycloalkyl group, an aryl group, an aralkyl group, an acyl group, a heterocyclic group, a heterocyclic alkyl group, a hydroxy group, an alkoxy group or an aryloxy group. Alternatively, $R^a$ and $R^b$ may be joined to form an aromatic ring or a cycloalkyl ring together with the carbon atoms to which they are attached respectively. Moreover, in formula (I), the bond between the carbon atoms to which $R^a$ and $R^b$ are attached respectively may be a single bond or a double bond, i.e., is not limited in any way. In formula (I), to express these two bonding modes collectively, the bond between these carbon atoms is represented by a combination of one solid line and one broken line.

$L^1$ represents NH, CO, a group represented by the following general formula (11):

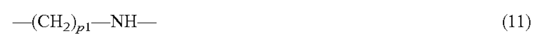

$$—(CH_2)_{p1}—NH— \quad (11)$$

(wherein p1 represents an integer of 1 to 6), or a group represented by the following general formula (12):

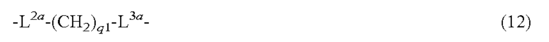

$$-L^{2a}-(CH_2)_{q1}-L^{3a}- \quad (12)$$

(wherein $L^{2a}$ represents OCO, OCONH, NHCO, NHCOO, NHCONH, CONH or COO, $L^{3a}$ represents NH or CO, and q1 represents an integer of 1 to 6).

In the above formula (1), m1 and m2 each independently represent an integer of 0 to 500 (provided that the sum of m1 and m2 represents an integer of 10 to 500), and m3, m4 and m5 each independently represent an integer of 1 to 5. In the above formula (1), n represents the number of repeating units (degree of polymerization) in the PEG moiety, and more specifically represents an integer of 1 to 500 (preferably 100 to 400, more preferably 200 to 300).

The molecular weight (Mn) of the cationic polymer represented by general formula (1) is not limited in any way, but it is preferably 23,000 to 45,000, and more preferably 28,000 to 34,000. With regard to the individual block moieties, the PEG moiety has a molecular weight (Mw) of preferably 8,000 to 15,000, and more preferably 10,000 to 12,000, while the polycation moiety as a whole has a molecular weight (Mn) of preferably 15,000 to 30,000, and more preferably 18,000 to 22,000.

The cationic polymer represented by general formula (1) may be prepared in any manner. For example, a segment comprising $R^1$ and the block moiety of PEG chain (PEG segment) is synthesized in advance, and given monomers are sequentially polymerized to one end (opposite to $R^1$) of this PEG segment, optionally followed by substituting or converting each side chain to contain a cationic group, or alternatively, the above PEG segment and a block moiety containing cationic groups in its side chains are synthesized in advance, which are then liked to each other. Procedures and conditions for each reaction in these preparation processes may be selected or determined as appropriate in consideration of standard processes.

In one embodiment of the present invention, the compound represented by formula (I) is at least one of compounds represented by the following formulae (Ia) to (Ig).

(Ia)

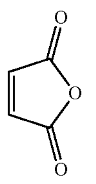

(Ib)

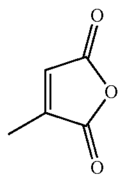

(Ic)

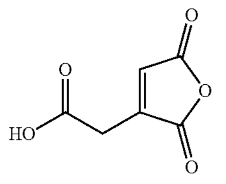

(Id)

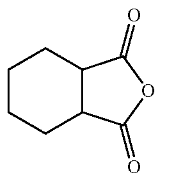

-continued (Ie)

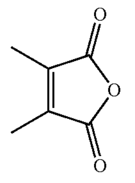

(If)

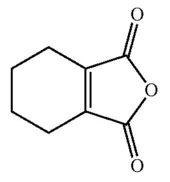

(Ig)

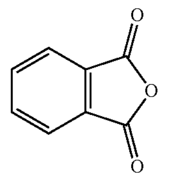

In a preferred embodiment of the present invention, the compound represented by formula (I) is a compound represented by the following formula (Ia) or (Ib).

(Ia)

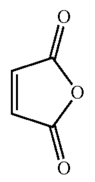

(Ib)

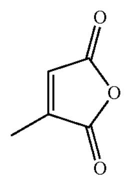

In formula (I), possible substituents may be saturated or unsaturated non-cyclic or cyclic hydrocarbon groups. In the case of non-cyclic hydrocarbon groups, they may be either linear or branched. Examples of such hydrocarbon groups include a $C_1$-$C_{20}$ alkyl group, a $C_2$-$C_{20}$ alkenyl group, a $C_4$-$C_{20}$ cycloalkyl group, a $C_6$-$C_{15}$ aryl group, a $C_6$-$C_{20}$ aralkyl group, a $C_1$-$C_{20}$ alkoxy group, and a $C_6$-$C_{18}$ aryloxy group.

The compound represented by formula (I) is used as a charge regulator. The compound represented by formula (I) acts to convert the charge of a basic or neutral protein as a whole into that of an acidic protein. In other words, the charge regulator of the present invention is deemed to cause overall charge conversion by controlling the amount of charge such that a protein whose overall charge is positive (+) or in neutral state is converted into a protein whose overall charge is negative (−). More specifically, the above overall charge conversion is accomplished as follows: the above compound represented by formula (I) or a derivative thereof is bonded to an amino group (i.e., a positively charged group) contained in a protein, whereby the protein is negatively charged as a whole. For this purpose, this bonding is accomplished, for example, as follows: the above compound represented by formula (I) is bonded (covalently bonded) to an amino group in a protein to form a structure as represented by the following formula (I').

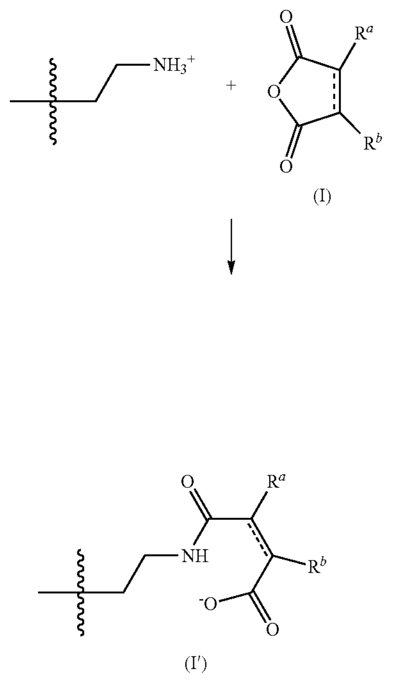

(I)

(I')

As to the above bonding, for example, when the above compound represented by formula (I) is a compound represented by formula (Ib) or (Ic) shown above, the above structure represented by formula (F) formed after the bonding is as shown below.

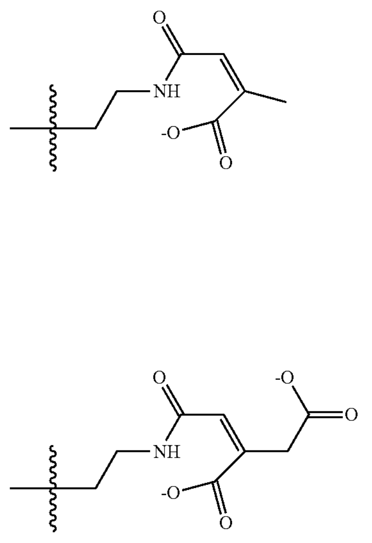

In a further embodiment of the present invention, the block copolymer represented by formula 1 is represented by the following formula 2.

(2)

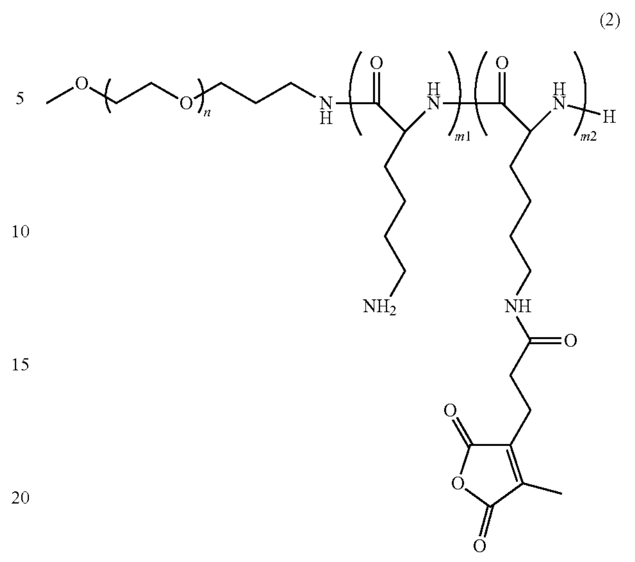

(2) Protein

In the PIC of the present invention, a protein serving as a member constituting the core region may be a protein whose charge has been converted as a whole by the above compound represented by formula (I) (i.e., a charge-conversional protein), and more specifically may be a protein whose overall charge has been converted from the overall charge of a basic or neutral protein (which is positive or in neutral state) into a negative charge, as in the case of the overall charge of an acidic protein. Such a protein whose overall charge has been converted into a negative charge can be regarded as an anionic substance (polyanion) when the protein is taken as a whole. Thus, upon electrostatic interaction with the polycation moiety in the above cationic polymer, such a charge-conversional protein can easily form a micellar complex which is inherently difficult to form with a basic or neutral protein.

The protein to be used in the present invention may be of any type, as long as it is originally among basic or neutral proteins. The protein to be used in the present invention encompasses not only simple proteins, but also glycoproteins and lipoproteins, etc. Moreover, the protein to be used in the present invention is not limited to those consisting of full-length amino acid sequences, and also encompasses their partial fragments and peptides, etc., as well as proteins consisting of two molecules (dimer) or more molecules, and fusion proteins formed between partial or full-length sequences thereof. Moreover, the protein to be used in the present invention is not limited to those composed of natural amino acids, and also encompasses modified proteins comprising at least some unnatural amino acids as constituent members. Furthermore, the protein to be used in the present invention also encompasses those modified as appropriate to have various labeling substances or the like, if necessary. Specific examples of the protein to be used in the present invention include, but are not limited to, heme proteins, various cytokines, various enzymes, or antibodies (e.g., antibodies against nuclear pore complexes) or antibody fragments, etc.

(3) Polyion Complex (PIC)

The PIC of the present invention can be regarded as a core-shell type micellar complex in such a state where the protein and a part (polycation moiety) of the above cationic polymer form a core region through their electrostatic interaction, and other parts (including the PEG moiety) in the cationic polymer form a shell region around the core region.

The PIC of the present invention may be readily prepared, for example, by mixing the protein and the cationic polymer in any buffer (e.g., Tris buffer). The mixing ratio between the cationic polymer and the protein is not limited in any way. However, in the present invention, for example, the ratio between the total number (N) of cationic groups (e.g., amino groups) in the block copolymer and the total number (C) of carboxyl groups in the protein (N/C ratio) may be set to 0.1 to 200, particularly 0.5 to 100, and more particularly 1 to 50. If the N/C ratio is within the above range, it is preferred in that free molecules of the cationic polymer can be reduced. It should be noted that the above cationic groups (N) are intended to mean groups capable of forming ionic bonds through electrostatic interaction with carboxyl groups in the protein to be enclosed within the micelle.

The PIC of the present invention is of any size. For example, its particle size is preferably 5 to 200 nm, and more preferably 10 to 100 nm, as measured by dynamic light scattering (DLS).

Upon introduction into cells, the PIC of the present invention will release the protein enclosed therein. In this case, the above compound represented by formula (I) is dissociated (cleaved) from the protein in response to a change in the pH environment within the cytoplasm (which is changed to a weakly acidic environment (e.g., around pH 5.5)). As a result, the charge (overall charge) of the protein as a whole returns to the original charge (overall charge) inherent to the protein, so that the protein can be present within the recipient cells in a state where its structure and activity, etc. are regenerated.

2. Protein Delivery Device

The present invention provides a protein delivery device comprising the above polyion complex (PIC). The protein delivery device of the present invention can be used as a means to efficiently introduce a desired protein (charge-conversional protein) enclosed within the core region of PIC into any site in target cells selected from a cell surface site, an intracellular site and an extracellular site, with the aid of changes in the oxidation-reduction environment between inside and outside of the cells.

More specifically, a solution containing PIC enclosing a desired protein is administered to an animal subject and taken up into target cells in the body. Then, once the PIC taken up into the cells has reached endosomes, the compound represented by formula (I) will be liberated from the protein to cause a change in the charge balance within the PIC, whereby the PIC will be broken down. Once the PIC has been broken down, the protein will be released from the PIC, and the polymer dissociated at the same time from the PIC will damage the endosomal membrane. As a result, the endosomes are destructed to achieve delivery of the released protein into the cytoplasm.

For example, in the case of micelles enclosing a cytokine such as IL-12, the protein is released outside of cells and binds to its receptor on the cell surface, so that delivery can be targeted to cell surface sites. In a case where an enzyme which is functional within cells is delivered by means of micelles, the protein is released inside of cells and functions as an enzyme, so that delivery can be targeted to intracellular sites. For antibody delivery, extracellularly secreted proteins may be targeted in some cases, so that delivery can be targeted to extracellular sites. Of course, delivery can also be targeted to combinations of two or three of these cell surface, intracellular and extracellular sites.

The protein delivery device of the present invention may be applied to various mammals including, but not limited to, humans, mice, rats, rabbits, pigs, dogs and cats. For administration to an animal subject, parenteral modes such as intravenous drip infusion are usually selected, and conditions (e.g., dosage, administration frequency and administration period) may be determined as appropriate for the type and condition of the animal subject.

The protein delivery device of the present invention can be used in therapies (e.g., enzyme replacement therapy, antibody-based immunotherapy) in which a desired protein is introduced into cells responsible for various diseases. Thus, the present invention can also provide a pharmaceutical composition (e.g., for enzyme replacement therapy or immunotherapy) containing the above PIC, as well as a method (e.g., enzyme replacement therapy or antibody-based immunotherapy) for treatment of various diseases using the above PIC. It should be noted that the administration mode and conditions are the same as those described above.

The above pharmaceutical composition may be prepared in a standard manner by using appropriately selected excipients, fillers, extenders, binders, wetting agents, disintegrants, lubricants, surfactants, dispersants, buffering agents, preservatives, solubilizers, antiseptics, correctives, soothing agents, stabilizers and isotonizing agents, etc., which are commonly used for drug preparation. Moreover, the pharmaceutical composition may usually be in the dosage form of intravenous injections (including drip infusions) and is provided in the form of unit dose ampules or multi-dose containers, by way of example.

3. Protein Delivery Kit

The protein delivery kit of the present invention is characterized by comprising the above block copolymer. This kit can be preferably used, for example, in various therapies using a desired protein (e.g., enzyme replacement therapy, antibody-based immunotherapy).

In the kit of the present invention, the cationic polymer may be stored in any state, and a solution or powder state may be selected in consideration of its stability (storage quality) and easiness of use, etc. The kit of the present invention may further comprise other components, in addition to the above block copolymer. Examples of other components include various buffers, various proteins to be introduced into cells (charge-conversional proteins), dissolution buffers, and instructions for use (instruction manual), etc. The kit of the present invention is used to prepare a polyion complex (PIC) whose core region is formed from a desired protein to be introduced into target cells, and the PIC thus prepared can be effectively used as a device for protein delivery into target cells.

EXAMPLES

The present invention will be further described in more detail by way of the following illustrative examples, which are not intended to limit the scope of the invention.

1. Materials and Methods 1.1. Materials

α-Methoxy-ω-amino-poly(ethylene glycol) (MeO-PEG-$NH_2$; Mn=12,000) was purchased from NOF corporation (Tokyo, Japan). N-Trifluoroacetyl-L-lysine N-carboxyanhydride (Lys(TFA)-NCA) was purchased from Chuo Kaseihin Co., Inc. (Tokyo, Japan). Oxalyl chloride, 2-propion-3-methylmaleic anhydride, dichloromethane ($CH_2Cl_2$), N,N-dimethylformamide (DMF), toluene, methanol and deuterium oxide (99.8 atom % D) were purchased from Tokyo Kagaku Kougyou Co., Ltd. (Tokyo, Japan). Alexa Fluor 647 NHS ester (Succinimidyl Ester) was purchased from Thermo Fisher (Waltham, MA, U.S.A.), DMSO-$d_6$ and Dulbecco's Modified Eagle Medium (DMEM) were purchased from Sigma Aldrich (St. Louis, MO, U.S.A.), and fetal bovine serum (FBS) was purchased from Dainippon Sumitomo Pharma Co., Ltd. (Osaka, Japan). Cell Counting Kit-8 (CCK-8) was purchased from Dojindo Laboratories (Kumamoto, Japan). Dialysis membranes were purchased from Spectrum Laboratories Inc. (Rancho Dominguez, CA, U.S.A.), and Vivaspin 6 Centrifugal Filter Unit (including 10,000 MWCO (molecular weight cut-off), 30,000 MWCO and 100,000 MWCO) was purchased from Sartorius (Gottingen, Germany).

1.2. Instruments

Proton nuclear magnetic resonance ($^1$H-NMR) spectra were obtained using a JEOL ECS-400 spectrometer (JOEL Ltd., Japan) with a frequency of 400 MHz, and chemical shifts were calculated as parts per million (ppm). The molecular weight distribution of a polymer was measured by gel permeation chromatography (GPC). Organic phase GPC was conducted on a TOSOH HLC-8220 system (Tosoh Corporation, Japan) equipped with TSK gel G4000$H_{HR}$ and G3000$H_{HR}$ columns, and poly(ethylene glycol) standards were used for calibration (Polymer Laboratories, Ltd., UK). Aqueous phase GPC measurement was conducted using a JASCO LC-EXTREMA system (JASCO, Japan) with a size exclusion column Superdex 200-10/300GL (GE Healthcare; U.S.A.) mounted thereon. Size distribution and zeta potential were measured with a Zetasizer Nano-ZS (Malvern, U.K.) through dynamic light scattering (DLS) and laser doppler electrophoresis, respectively. Fluorescence intensity from fluorescamine assay was measured through a ND-3300 nanodrop fluorescence spectrometer (Thermo Fisher, U.S.A.). UV/Vis spectrophotometry was conducted with a V-500 spectrophotometer (JASCO, Japan).

1.3. Synthesis of PEG-Poly(L-Lysine-CDM) Block Copolymer

A PEG-poly(L-lysine) block copolymer (PEG-p(Lys)) was prepared as follows, in accordance with the previously reported procedures[20] with minor modifications.

MeO-PEG-$NH_2$ (Mn=12,000) was reacted with Lys (TFA)-NCA to form PEG-p(Lys-TFA) through ring-opening polymerization, followed by deprotection of the trifluoroacetyl groups. In brief, MeO-PEG-$NH_2$ (1 g, 0.083 mmol) and Lys(TFA)-NCA (1.005 g, 3.75 mmol) were dissolved separately in 1 M thiourea containing DMF, and the NCA solution was then transferred to the PEG solution under an argon atmosphere and stirred at 35° C. for 3 days. The polymer was collected as a white powder by being precipitated in diethyl ether and dried under vacuum. The degree of polymerization was determined by $^1$H-NMR spectrometry (DMSO-$d_6$, 80° C.), while the molecular weight distribution was analyzed by GPC (mobile phase: 10 mM LiCi containing DMF; temperature: 40° C.; flow rate: 0.8 mL/min; detector: refractive index). Further, the protecting groups (TFA) were removed by being treated overnight at 35° C. with a 1 M NaOH methanol solution and then dialyzed against water using a dialysis membrane with a MWCO of 6 to 8 kD. After lyophilization, the final product was obtained as a white powder. The deprotected polymer was analyzed for its components by $^1$H-NMR spectrometry ($D_2O$, 25° C.). In the $^1$H-NMR spectrum, the intensity ratio between peaks derived from protons in —$OCH_2CH_2$ of PEG and in —$C_3H_6$ of lysine was calculated to determine the composition of the PEG-p(Lys) block copolymer. The molecular weight distribution was analyzed by GPC (mobile phase: acetate buffered saline (pH 3.3) of 10 mM acetate and 500 mM NaCl; room temperature; flow rate: 0.75 mL/minute; detector: UV, at a wavelength of 220 nm).

PEG-p(Lys-CDM) was prepared by reacting an acyl chloride of CDM with PEG-p(Lys). First, an acyl chloride of CDM (CDM-Cl) was prepared in accordance with the previously reported procedures[21] with minor modifications. 2-Propion-3 -methylmaleic anhydride (CDM, 200 mg, 1.09 mmol) was dissolved in anhydrous toluene and evaporated under vacuum. CDM was dissolved in anhydrous $CH_2C_2$ (15 mL), and oxalyl chloride (4 mL, 5.9 g, 46 mmol) was then added thereto and reacted with CDM at room temperature for 12 hours. Then, $CH_2Cl_2$ and residual oxalyl chloride were removed by evaporation to obtain a transparent oil. Subsequently, $CH_2Cl_2$ (4 ml) was added to dissolve CDM-Cl, while PEG-p(Lys) (200 mg, 0.011 mmol) was dissolved with $CH_2Cl_2$ (20 ml). Then, the PEG-p(Lys) solution was transferred to the CDM-Cl solution, and the reaction mixture was stirred at room temperature. After 12 hours, the product was collected by diethyl ether precipitation and overnight vacuum drying. The final product was analyzed by $^1$H-NMR and GPC.

S1. Chemical reaction scheme, polymer synthesis and chemical analysis

Scheme S1. Synthesis schemes of acyl chloride-CDM and PEG-p(Lys-CDM) block copolymer.

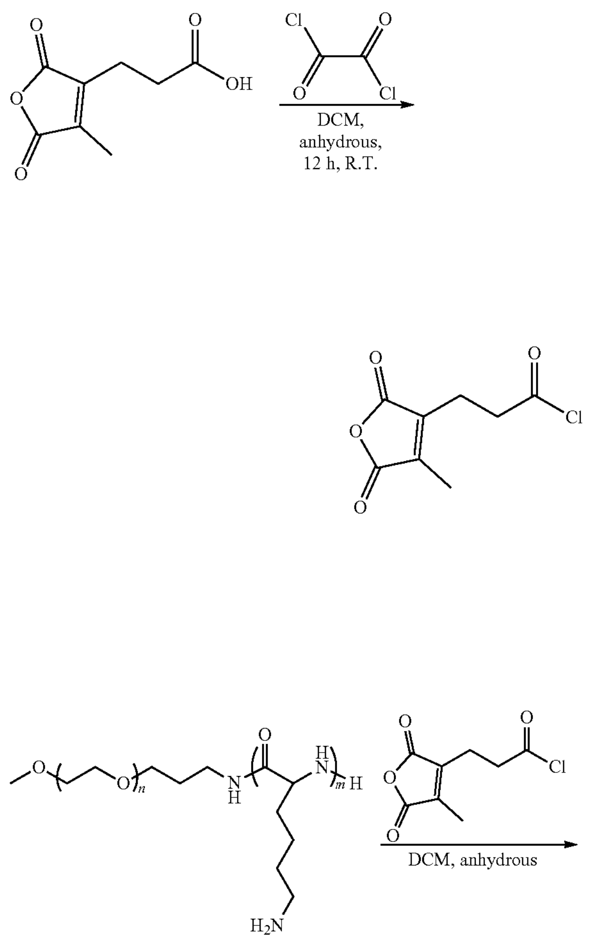

-continued

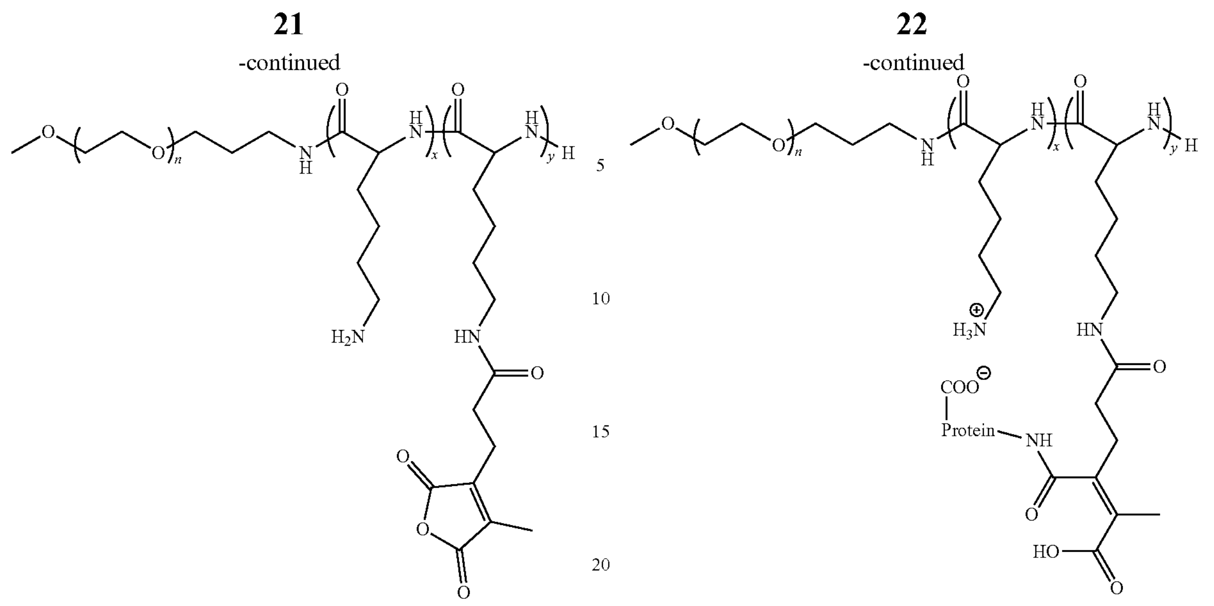

-continued

In Scheme S1, n=272, m=37, x=20, and y=17.

Scheme S2. CDM derivative is reacted with an amino group to form an amide bond and generate a carboxyl group.

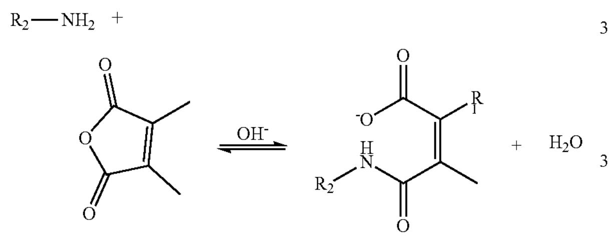

Scheme S3. PEG-p(Lys-CDM) forms PIC with a carboxyl group in a protein, and is covalently bonded to an amino group in the protein through the pH-responsive CDM moiety.

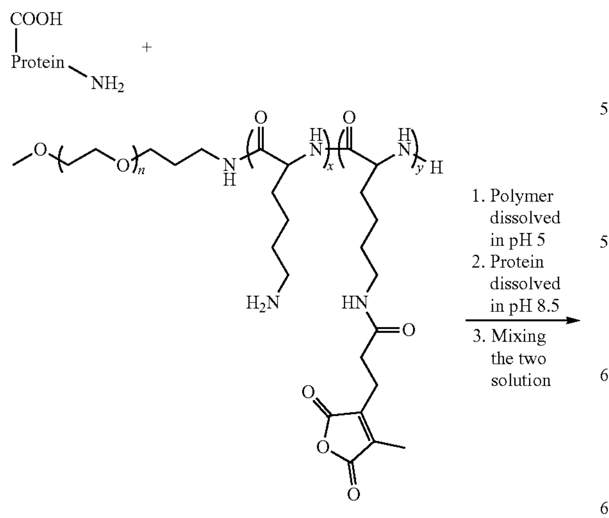

In Scheme S3, n=272, m=37, x=20, and y=17.

1.4. Preparation of Core-Crosslinked Polyion Complex (PIC) Micelles Enclosing No Protein (Empty PIC Micelles), and their Stability Under Various pH Conditions A polymer solution (1 mg/mL) was prepared in acetate buffer of pH 4 or 5 or in phosphate buffer of pH 6.5 or 7.4 (i.e., in 10 mM acetate or phosphate containing 150 mM NaCl). The polymer was dissolved in buffers of different pHs (vortexed for 1 minute and incubated for 1 hour). The solutions were each filtered through a 0.22 μm syringe filter, followed by DLS measurement. In addition, a polymer solution was prepared in deuterated phosphate buffer (10 mM) at pH 7.4, and analyzed by $^1$H-NMR spectrometry before and after addition of deuterated hydrochloric acid (DCl).

Further, empty PIC micelles autonomously associated in the buffer of pH 7.4 were allowed to stand in 10 mM phosphate buffer of pH 6.5 or 7.4 containing 150 mM NaCl at a final polymer concentration of 0.5 mg/ml, and the empty PIC micelles were evaluated over time by DLS for their stability under these conditions. Their intensity-based size distribution, polydispersity index (PDI) and derived count rate were evaluated.

1.5. In Vitro Cytotoxicity

PEG-p(Lys-CDM) was evaluated for its in vitro cytotoxicity against human fetal kidney cell line 293 (HEK 293). In this experiment, PEG-p(Lys) was used as a control. These cells were seeded with 10% FBS-containing DMEM medium on 96-well plates at 3000 cells per well, and incubated under 5% $CO_2$ at 37° C. for 24 hours. Then, the cells were exposed to the polymer at various concentrations. After 48 hour incubation with the polymer, the cytotoxicity was evaluated by CCK-8 assay designed to measure the absorbance of formazan at 450 nm. Further, the PEG-p(Lys-CDM) block copolymer was dissolved in DMEM (vortexed for 1 minute and incubated for 1 hour), and the resulting solution was evaluated by DLS.

1.6. Preparation of Myoglobin-Enclosing Micelles (Myo/m) and their Physicochemical Evaluation The PEG-p(Lys-CDM) polymer (3 mg/mL) was dissolved in a buffer of pH 5 (10 mM acetate) to prevent empty PIC micelle formation, and a solution of 0.1 molar equivalents of myoglobin was prepared in a buffer (10 mM phosphate, pH 8). After these two solutions were mixed, the resulting solution was adjusted to pH 7.4 and then stirred for 6 hours. Then, the solution was ultrafiltered through a centrifugal filter with a MWCO of 100,000 using phosphate buffered saline of pH 7.4 (10 mM phosphate containing 150 mM NaCl), whereby micelles were purified and non-bonded protein and polymer molecules were removed. Further, for evaluation of enclosure efficiency, myoglobin was labeled with Alexa Fluor 647 succinimidyl ester, and the mixed solution was analyzed by GPC (mobile phase: 10 mM phosphate buffer of pH 7.4 containing 150 mM NaCl; flow rate: 0.75 mL/minute; room temperature).

For fluorescence detection, an excitation wavelength of 650 nm and an emission wavelength 668 nm were used. The enclosure efficiency was calculated by dividing the amount of protein enclosed by the amount of protein added. Further, the amount of Alexa Fluor 647-labeled myoglobin enclosed per micelle was quantified by fluorescence correlation spectroscopy (FCS). The FCS experiment was conducted at room temperature by using a MF-20 system (Olympus Corporation, Japan) equipped with a laser beam of 633 nm wavelength. Further, lysozyme and albumin were also enclosed within micelles in the same manner, and their micelle size was determined by DLS.

1.7. Preparation of CDM-Modified Myoglobin-Enclosing Micelles (CC-Myo/m) and their Physicochemical Evaluation CDM-modified myoglobin (CC-myo)-enclosing micelles (CC-myo/m) were prepared as control micelles in accordance with the previously reported procedures[14,16] with minor modifications. In brief, myoglobin was dissolved in 0.1 M $NaHCO_3$ buffer to prepare a 2 mg/mL solution, which was then stirred at 4° C. for 30 minutes. Then, 50 molar equivalents of CDM was slowly added to the solution, followed by stirring at 4° C. for 2 hours. This myoglobin solution was purified by ultrafiltration through a centrifugal filter with a MWCO of 10,000. The efficiency of CDM modification was determined by the fluorescamine method with a Nanodrop fluorescence spectrometer (Thermo Fisher, U.S.A.), and the proportion of the converted amine was calculated in accordance with the previously reported procedures[16]. Subsequently, PEG-p(Lys) was mixed with the charge-converted myoglobin to prepare CC-myo/m, followed by titration at an N/C (amino group/carboxyl group) ratio of 2:1 into phosphate buffered physiological saline of pH 7.4. Further, a mixture of PEG-p(Lys) and native myoglobin was used as a control at the same polymer to protein molar equivalent ratio. The size distribution, polydispersity index (PDI) and zeta potential of these micelles were analyzed with a Zetasizer Nano ZS.

1.8. Stability of Myoglobin-Enclosing Micelles in Buffers of Different Salt Concentrations and Different pHs To test myo/m and CC-myo/m for their in vitro stability under different pH conditions, samples were each diluted to give a polymer concentration of 0.5 mg/mL. The micelles were incubated in 10 mM phosphate buffer of pH 6.5 or pH 7.4 containing 150 mM NaCl solution, and measured over time by DLS (25° C.). The size distribution, PDI and derived count rate obtained were recorded on a Zetasizer Nano ZS. Further, a high concentration salt buffer was used to block electrostatic interaction, and the micelles were examined for their stability. myo/m and CC-myo/m were prepared and diluted to give a polymer concentration of 0.5 mg/mL. Each micelle solution was dialyzed against 5 L of 10 mM phosphate buffer of pH 7.4 or pH 6.5 containing 600 mM NaCl in a dialysis cassette with a MWCO of 20,000. At different time points, samples were taken from the inside of the dialysis cassette to monitor the breakdown of micelles by DLS-based analysis.

1.9. Myoglobin Release from Myo/m Under Different pH Conditions

Using a dialysis cassette with a MWCO of 20,000 Da, Alexa Fluor 647-labeled myo/m were dialyzed against 5 L of 10 mM phosphate buffer and 150 mM NaCl at pH 7.4 or pH 6.5 at room temperature. Samples were taken from the inside of the dialysis cassette at given time points and evaluated for fluorescence intensity with a NanoDrop 3300 fluorescence spectrometer.

1.10. Evaluation of Myoglobin Activity

Myoglobin was released from micelles by overnight incubation at pH 6.5 under dilution conditions of 10 mM phosphate buffer+150 mM NaCl, and the subsequent ultrafiltration through a centrifugal filter with a MWCO of 30,000. The filter passing fraction was collected and then concentrated to 0.05 mg/mL by ultrafiltration through a centrifugal filter with a MWCO of 10,000. Myoglobin activity was evaluated on the basis of the previously reported procedures[22]. Spectrophotometry was conducted with a UV/Vis spectrometer using a quartz cuvette of 1 cm optical length. The released myoglobin (0.05 mg/mL) was reduced by addition of 5 equivalents of aqueous sodium dithionite ($NaS_2O_4$). Subsequently, the reduced myoglobin was oxidized by introduction of $O_2$ for 30 minutes, and then further reduced by bubbling with argon for 2 hours. This oxidation/reduction cycle was repeated several times in accordance with the previously reported protocols[22]. As a control, the same concentration of native myoglobin was used.

1.11. In Vivo Blood Retention and In Vivo Distribution

Alexa Fluor 647-labeled myoglobin was used to prepare myo/m, CC-myo/m and free myoglobin, and the blood retention and in vivo distribution of myoglobin were monitored under a Nikon AIR in vivo confocal laser scanning microscope (IV-CLSM) (Nikon Corporation, Japan). Balb/c female mice at 5 weeks of age were each injected with 100 μL of a sample solution containing 100 μg/mL fluorescently labeled myoglobin through the tail vein under anesthesia, and then observed for their ear lobe capillaries[23]. Fluorescence intensities in the ear lobe vein and skin were continuously measured. At 12 hours after injection, the mice were euthanized, and their organs (kidney, liver and spleen) were extracted and then imaged ex vivo under IV-CLSM. It should be noted that at 30 minutes before euthanasia and organ extraction, 100 μL of a Hoechst 33342 solution was administered through the tail vein for nuclear staining. Further, Alexa Fluor 647-labeled polymer and non-labeled myoglobin were used to prepare myo/m and CC-myo/m for monitoring the blood retention of the polymer in these micelles in blood. Mice were each administered with 100 μL of a sample solution containing 2 mg/mL fluorescently labeled polymer through the tail vein, and their ear lobe capillaries were imaged under the microscope. It should be noted that all animal experiments in this test were carried out in compliance with the laboratory animal management rules of the University of Tokyo.

1.12. Labeling of Protein and Polymer

Protein labeling with Alexa Fluor 647 succinimidyl ester was accomplished in accordance with the manufacturer's protocol with minor modifications. In brief, 5 mg/ml protein was dissolved in 0.15 M sodium bicarbonate buffer, while 0.5 molar equivalents of Alexa Fluor 647 succinimidyl ester was dissolved in DMF to prepare a 10 mg/ml solution. The above two solutions were mixed and reacted at room temperature for 1 hour. Then, the resulting solution was applied to a Sephadex G-25 column and purified by gel permeation chromatography. After purification, the Alexa Fluor 647-labeled protein was lyophilized for further use. PEG-p(Lys) labeling and purification were conducted in the same manner as protein labeling and purification. However, PEG-p(Lys-CDM) has self-assembling properties; and hence its labeling was conducted in 10 mM phosphate buffer (pH 6.5), followed by gel filtration for free dye removal, and the polymer solution was then treated with 0.1 N HCl for 5 minutes and immediately lyophilized.

1.13. Fluorescence Correlation Microscope

A fluorescence correlation spectroscopy (FCS) experiment was conducted at room temperature on a MF-20 system (Olympus Corporation, Japan) equipped with a laser beam of 633 nm wavelength. Alexa Fluor 647-labeled myoglobin and Alexa Fluor 647-labeled myoglobin-enclosing micelle solutions were dispensed into pre-treated 384-well glass bottomed microplates in a volume of 30 μL/well. For structural parameter determination, a standard 633 nm solution with a molecular weight of 652 Da (Olympus Corporation, Japan) was also dispensed into the plates. Each sample was excited with a 633 nm laser beam, and scanned five times for 20 seconds each. The resulting data were fitted with the aid of the software's automatic fitting function.

Figure 11:
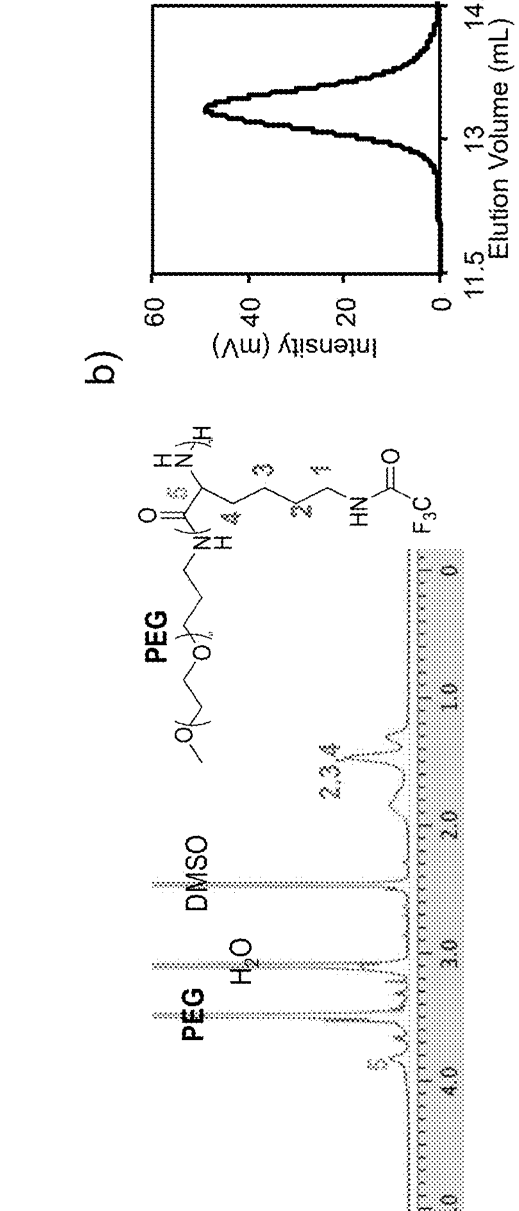
FIG. 11 shows the chemical analysis of PEG-p(Lys-TFA). a) $^1$H-NMR spectrum of PEG-p(Lys-TFA) in DMSO-$d_6$, b) GPC chromatogram of PEG-p(Lys-TFA), indicating a unimodal peak and a narrow molecular weight distribution (Mw/Mn=1.03) (flow rate: 0.8 mL/minute, mobile phase: a 10 mM LiCl-containing DMF solution).
Figure 12:
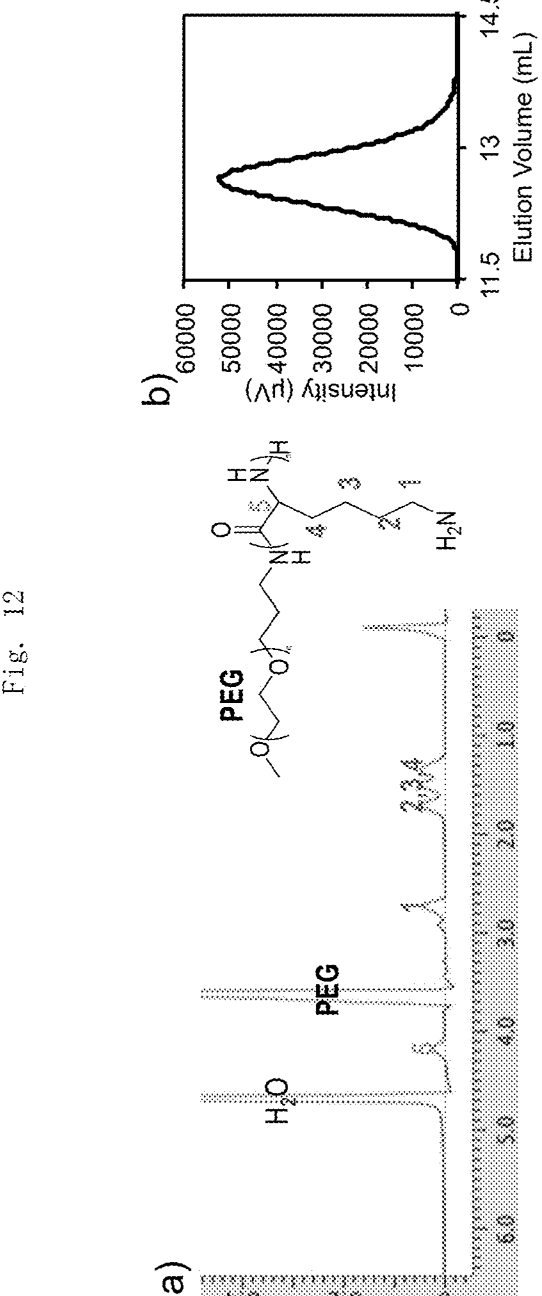
FIG. 12 shows the chemical analysis of PEG-p(Lys). a) $^1$H-NMR spectrum of PEG-p(Lys) in $D_2O$, b) GPC chromatogram of PEG-p(Lys) (flow rate: 0.75 mL/minute, mobile phase: acetate buffered saline (pH 3.3) of 10 mM acetate and 500 mM NaCl).

2. Results and Discussion 2.1. Synthesis and Chemical Analysis of Block Copolymer The PEG-p(Lys-TFA) polymer was synthesized through ring-opening polymerization of Lys(TFA)-NCA using the terminal primary amino group of MeO-PEG-$NH_2$[20] as an initiator. The polymer thus polymerized showed a narrow molecular weight distribution ($M_w/M_n$=1.03), as analyzed by GPC (FIG. 11). After alkaline hydrolysis to remove the TFA protecting groups, the degree of polymerization (DP) was confirmed by $^1$H-NMR based on the proton ratio between —$OCH_2CH_2$— in PEG (δ=3.5 ppm) and —$C_3H_6$ in p(Lys) (δ=1.2 ppm to 1.8 ppm), thus indicating that the DP of lysine was 37. Further, PEG-p(Lys) showed a unimodal peak with a narrow molecular weight distribution, as analyzed by GPC (mobile phase: pH 3.3 acetate buffered saline of 10 mM acetate containing 500 mM NaCl; flow rate: 0.75 mL/minute) (FIG. 12).

Figure 13:
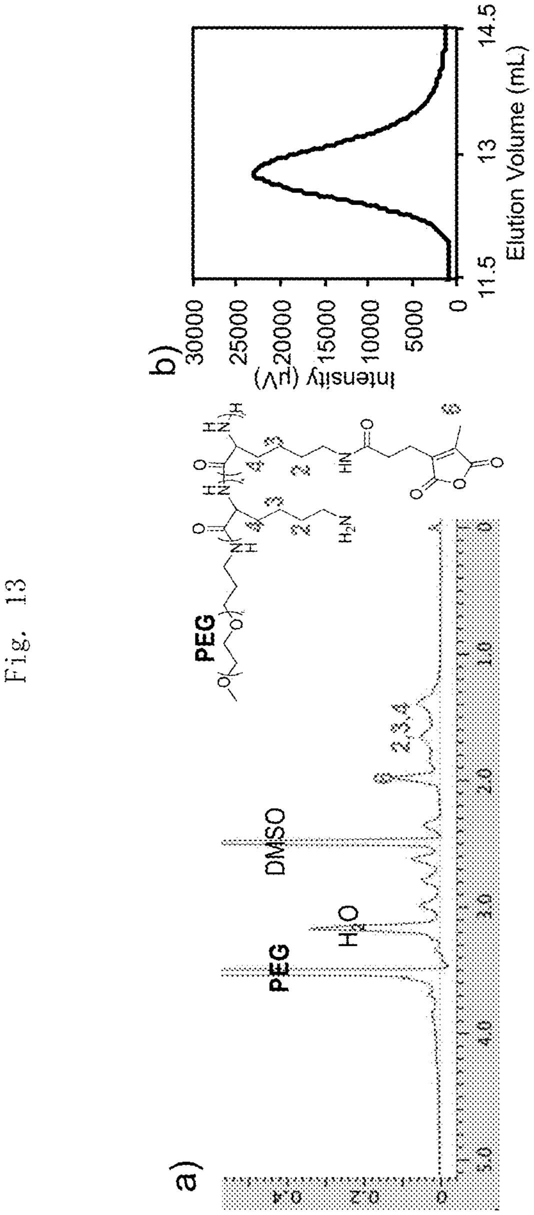
FIG. 13 shows the characterization of PEG-p(Lys-CDM). a) $^1$H-NMR spectrum of PEG-p(Lys-CDM) in DMSO-$d_6$, b) aqueous phase GPC chromatogram of PEG-p(Lys-CDM) (flow rate: 0.75 mL/minute, eluent: acetate buffered saline (pH 3.3) of 10 mM acetate and 500 mM NaCl)

Then, CDM-Cl was reacted with primary amines in PEG-p(Lys) to introduce CDM into the polymer. Moreover, the peak intensity of —$CH_3$ on CDM (δ=2.0 ppm) was compared with the methylene peak on PEG and β, γ and δ-methylene protons in lysine to confirm the amount of CDM introduced and the introduction rate thereof. CDM units were calculated to be about 17, and the addition rate of CDM was about 45%. Moreover, PEG-p(Lys-CDM) showed a narrow molecular weight distribution, as analyzed by GPC using an acetate buffer solution of pH 3.3 (10 mM acetate containing 500 mM NaCl) as a mobile phase (FIG. 13). These results indicate that PEG-p(Lys-CDM) was able to be synthesized at the level of quality required for micelle preparation.

2.2. Preparation of Core-Crosslinked Polyion Complex (PIC) Micelles Enclosing No Protein (Empty PIC Micelles), and their Stability Under Various pH Conditions Because of having both the amine moiety and the amine-reactive CDM unit, PEG-p(Lys-CDM) may probably be in the form of a free polymer under an acidic pH environment due to amine protonation and CDM ring formation. On the other hand, at apH close to neutral, the CDM group forms a stable amide bond with an amine to generate a carboxyl group for further polyion complex formation (Scheme S2). Thus, the inventors of the present invention evaluated the structure of PEG-p(Lys-CDM) by DLS after the polymer was incubated for 1 hour at different pHs.

Figure 2:
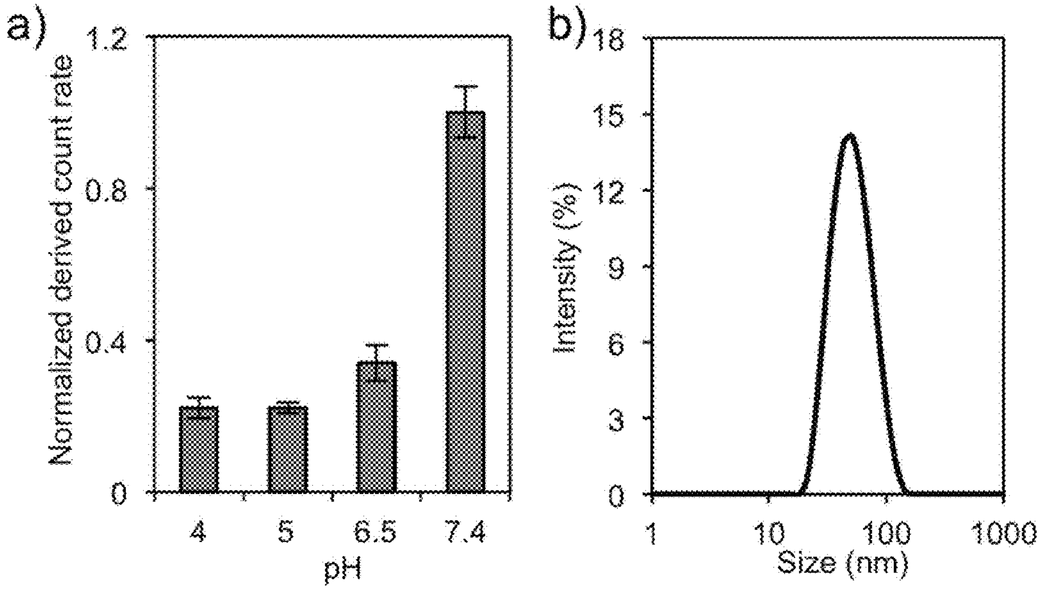
FIG. 2 shows the self-organization of PEG-p(Lys-CDM) in buffers of different pHs. a) Derived count rate normalized by the derived count rate of PEG-p(Lys-CDM) at pH 7.4. PEG-p(Lys-CDM) was added at a concentration of 1 mg/mL to 10 mM acetate buffer containing 150 mM NaCl (pH 4 or pH 5) or to 10 mM phosphate buffer containing 150 mM NaCl (pH 6.5 or pH 7.4), and then vortexed for 1 minute and incubated for 1 hour, followed by DLS measurement. The data are shown as mean±standard deviation (n=3). b) Particle size distribution of Empty-PIC micelles (empty micelles) formed at pH 7.4.
Figure 14:
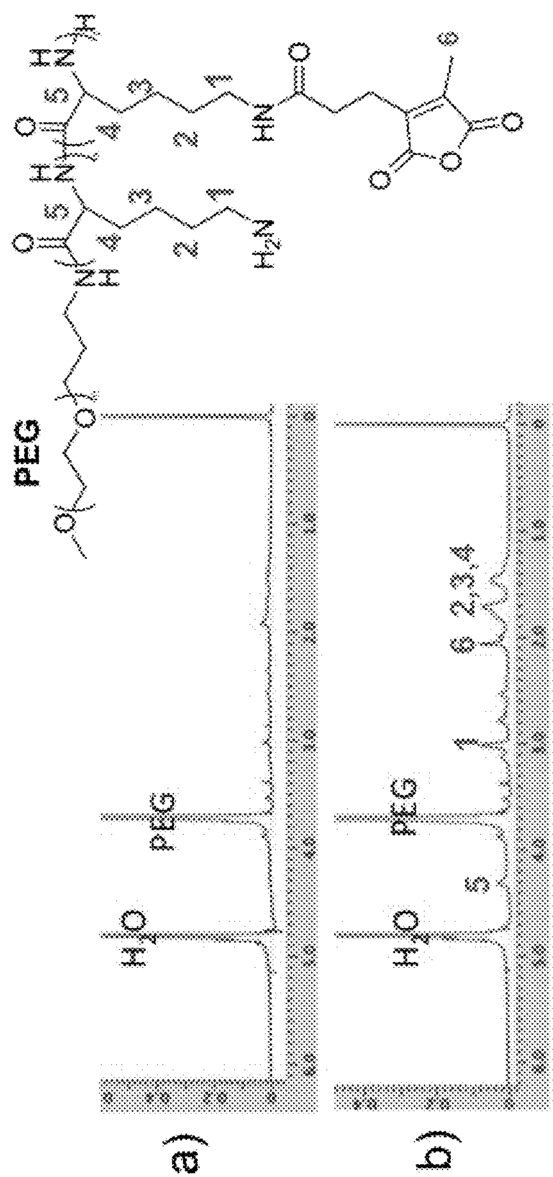
FIG. 14 shows the characterization of PEG-p(Lys-CDM). a) $^1$H-NMR spectrum (25° C., pH 7.4) of PEG-p(Lys-CDM) in 10 mM deuterated phosphate buffer (0.70 ml). The intensities of peaks derived from protons in the polyamino acid were lower than would be expected from the peak derived from protons in PEG, probably because the mobility of protons in the polymer was restricted by micelle formation. b) $^1$H-NMR spectrum of PEG-p(Lys-CDM) after addition of 2 M deuterated hydrochloric acid (volume ratio 1:35) and incubation for 10 minutes. Upon acid treatment, the intensities of peaks derived from protons in the polyamino acid were recovered to about 75%, thus suggesting that the mobility of protons in the polymer was increased by micelle breakdown under acidic conditions.

PEG-p(Lys-CDM) was found to autonomously associate into a micelle at pH 7.4 (higher than other pHs). The derived count rate is determined by DLS, which is correlated with the presence of large particles or high concentration particles [24] (FIG. 2*a*). The resulting micelles showed a size of about 40 nm and a PDI of 0.2 at pH 7.4. On the other hand, the derived count rate remained low at a pH less than 6.5, which indicates that PEG-p(Lys-CDM) did not associate into a micelle. $^1$H-NMR of the polymer in deuterated phosphate buffer (10 mM) of pH 7.4 was measured to find out the disappearance of proton peaks derived from the polyamino acid and the side chain structure in PEG-p(Lys-CDM), which indicates reduced mobility of the polyamino acid backbone due to bonding between amine and CDM moieties (FIG. 14*a*). After addition of 2 M deuterated hydrochloric acid to the above solution, the peaks from the polyamino acid and the side chain structure were recovered to 75% during incubation for 10 minutes (FIG. 14*b*). This indicates the dissociation of the polyamino acid under low pH conditions. Attention should be paid to pH-dependent micelle formation of PEG-p(Lys-CDM) in order to avoid the formation of empty micelles before protein addition.

Figure 3:
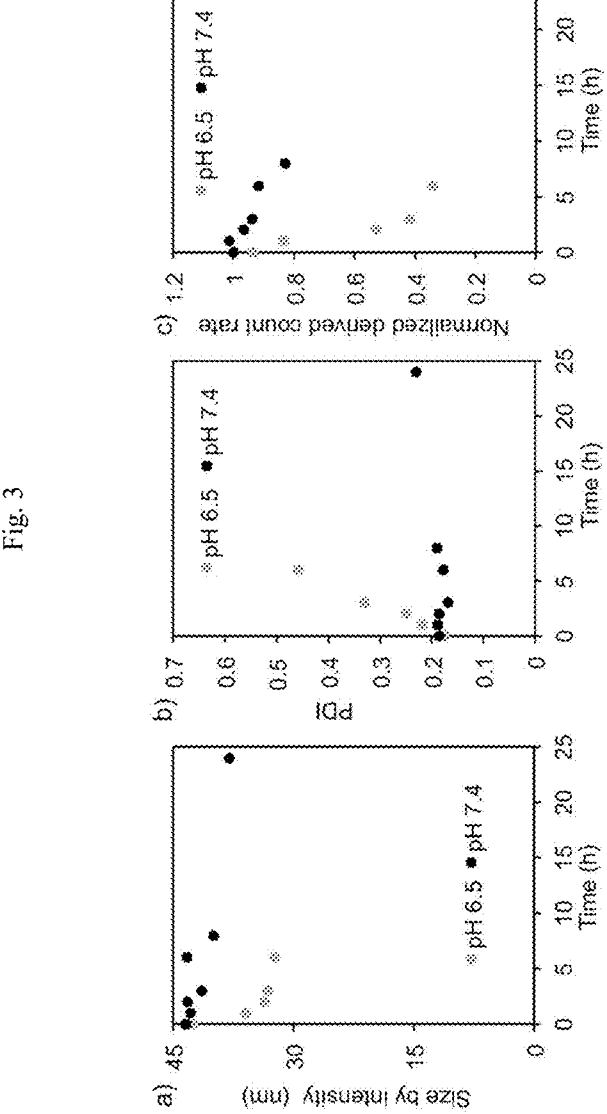
FIG. 3 shows the stability of empty micelles prepared in a buffer of pH 7.4. Empty micelles were added to 10 mM phosphate buffer containing 150 mM NaCl (pH 6.5 (gray dots) or pH 7.4 (black dots)) and adjusted to give a final concentration of 0.5 mg/mL, followed by DLS measurement. a) Particle size, b) PDI, and c) Derived count rate normalized by the derived count rate before dilution.

The stability of empty PIC micelles autonomously associated at pH 7.4 was evaluated by DLS after the micelles were diluted in solutions of different pHs. At pH 7.4, the size of empty PIC micelles was reduced from 43 nm to 38 nm for 24 hours (FIG. 3), the variation in PDI was small, and the derived count rate was attenuated by only 20%. On the other hand, at pH 6.5, empty PIC micelles were unstable and showed rapid reductions in their size and derived count rate, and further showed an increase above 0.4 in their PDI for the first 5 hours of incubation (FIG. 3). At pH 6.5, the micelle size measured after 5 hours was unreliable due to high PDI, and was therefore omitted. These results indicate that empty PIC micelles are broken down in response to pH.

2.3. In Vitro Cytotoxicity of PEG-p(Lys-CDM) Against HEK293 Cells

For the biomedical application of protein-enclosing micelles, it is important to determine whether PEG-p(Lys-CDM) can be used safely as a delivery carrier. For this purpose, PEG-p(Lys-CDM) was cultured together with HEK 293 cells for 48 hours to examine the cytotoxicity of PEG-p(Lys-CDM). The PEG-p(Lys) polymer was used as a control because it is a precursor of PEG-p(Lys-CDM) and is widely used as a delivery carrier.

Figure 4:
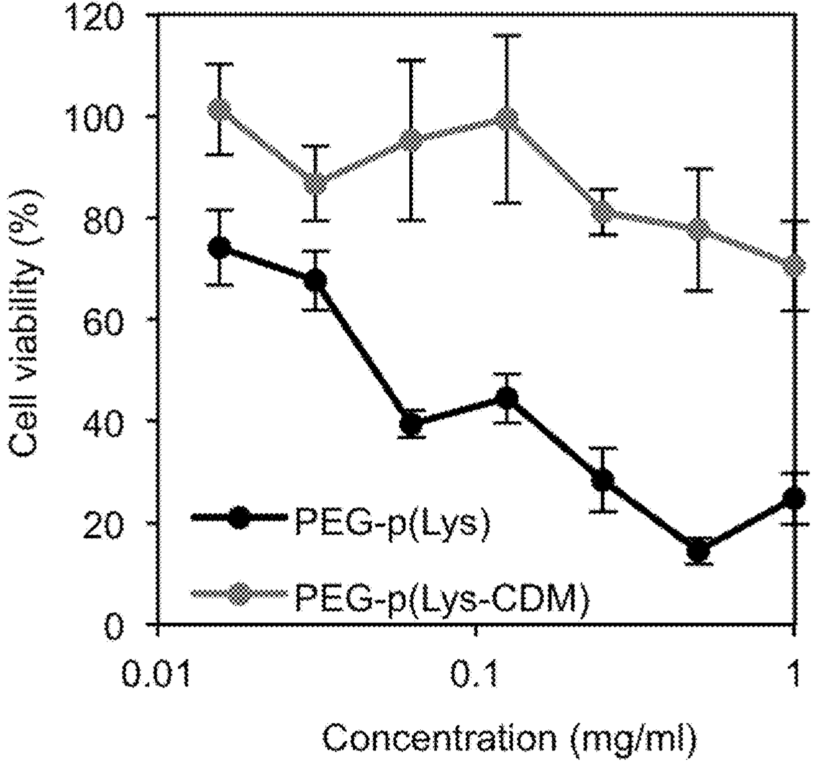
FIG. 4 shows the in vitro cytotoxicity of PEG-p(Lys-CDM) (gray line) against HEK 293 cells (obtained after the cells were cultured for 48 hours at different polymer concentrations). PEG-p(Lys) (black line) was used as a control. The data are shown as mean±standard deviation (n=4).
Figure 15:
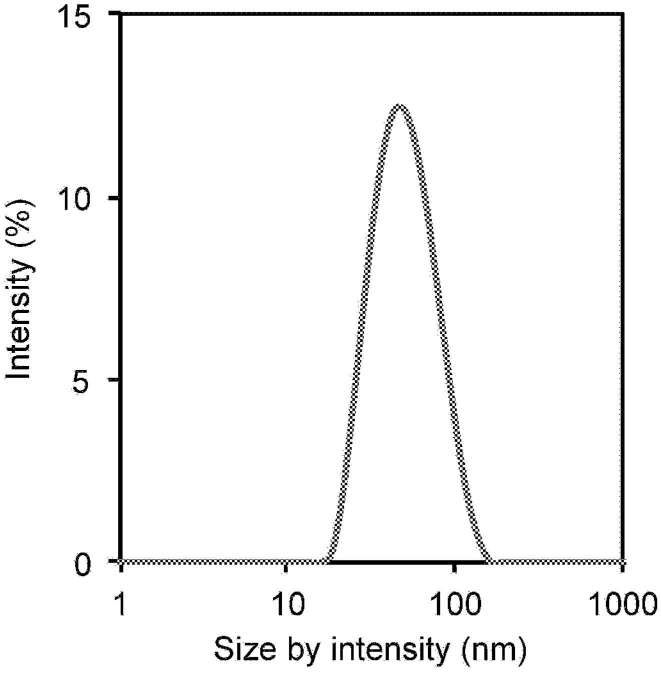
FIG. 15 shows the size distribution of 1 mg/mL PEG-p (Lys-CDM) in DMEM.

As shown in FIG. 4, PEG-(Lys-CDM) showed low cytotoxicity at all polymer concentrations when compared to PEG-p(Lys), and maintained 70% or more cell viability even at a polymer concentration of 1 mg/mL. The low toxicity of PEG-(Lys-CDM) is deemed to be due to its autonomous association into empty PIC micelles under medium conditions, as indicated by DLS evaluation of PEG-(Lys-CDM) in DMEM (FIG. 15). These results indicate that PEG-p(Lys-CDM) is a highly safe delivery carrier.

2.4. Preparation of Protein-Enclosing Micelles by Precise Control of pH

A protein is a macromolecule having a nonuniformly charged surface with many negatively charged groups (glutamic acid, aspartic acid, and the C-terminal carboxyl group) and positively charged groups (lysine, arginine, and the N-terminal amine). Thus, PEG-p(Lys-CDM) forms PIC with a carboxyl group in a protein, and can be covalently bonded to a primary amino group in the protein through the pH-responsive CDM moiety (Scheme S3). Further, amines in PEG-p(Lys-CDM) are reacted with CDM groups not bonded to the protein, which allows further crosslinking of the micelle core.

As observed as above (FIG. 2), PEG-p(Lys-CDM) can autonomously associate into a micelle at the medium pH. Since PEG-p(Lys-CDM) is present as a free polymer at pH 5, PEG-p(Lys-CDM) was dissolved in 10 mM acetate buffer (pH 5) to prepare a polymer solution, thereby preventing the formation of empty PIC micelles. Further, a protein solution was prepared in 10 mM phosphate buffer (pH 8) and mixed with the above polymer solution to cause polyion complex formation with lysine residues in PEG-p(Lys-CDM) and self-organization through amide formation with the CDM moiety. After the polymer solution and the protein solution were mixed, pH was adjusted to 7.4. Since free protein molecules and micelles showed different elution times in GPC, the enclosure efficiency of myoglobin was determined by GPC. Myoglobin was fluorescently labeled with Alexa Fluor 647 for fluorescence detection. The enclosure efficiency was calculated by dividing the amount of protein enclosed by the amount of protein added.

As shown in Table 1, myoglobin (which is a 17.6 kDa protein with an isoelectric point of 7) was enclosed within micelles with an efficiency of 62% and in an amount of 5% by weight, thus obtaining micelles of 40 nm size with a PDI of 0.18. The micelles were purified by ultrafiltration using phosphate buffered physiological saline (pH 7.4, 10 mM phosphate buffer containing 150 mM NaCl), followed by FCS to quantify the number of myoglobin molecules enclosed per micelle. The ratio of derived count rates per molecule was calculated between the micelles and Alexa Fluor 647-labeled myoglobin, thereby confirming that about two Alexa Fluor 647-labeled myoglobin molecules were enclosed per micelle (Table 2).

TABLE 1

Characteristics of myo/m and control micelles

| Micelle | Protein/derivative | Polymer | Size (nm)[a] | PDI[b] | ζ potential (mV)[c] |
|---|---|---|---|---|---|
| Myo/m | Myoglobin | PEG-p(Lys-CDM) | 40 | 0.18 | −2.1 |
| CC-myo/m | CC-myo | PEG-p(Lys) | 55 | 0.12 | −0.11 |
| Myo-m(PIC) | Myoglobin | PEG-p(Lys) | 678 | N.D.[d] | N.D.[d] |

[a]Z-average size (determined by DLS)
[b]determined by DLS
[c]determined by light scattering electrophoresis
[d]not determined

TABLE 2

Results of FCS measurement for Alexa Fluor 647-labeled myoglobin-enclosing micelles and free myoglobin

| Sample name | Counts per particle ± S.D. (kHz)[a] | Diffusion time ± S.D. (μs)[a] |
|---|---|---|
| Alexa Fluor 647-myoglobin-enclosing micelle | 27.1 ± 0.4 | 2510.4 ± 160.4 |
| Alexa Fluor 647-myoglobin | 14.3 ± 0.3 | 501.1 ± 10.8 |

[a]determined by FCS

Figure 16:
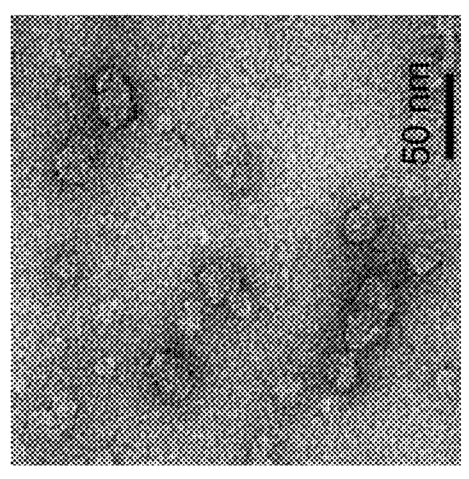
FIG. 16 shows TEM images of micelles enclosing lysozyme (left), myoglobin (middle) and BSA (right). Scale bar: 50 nm. The morphology of micelles was observed under TEM (JEM-1400, JEOL). The protein-enclosing micelles were stained with phosphotungstic acid (PTA) (2%, w/v) and mounted on 400 mesh copper grids. Images were taken at a magnification of 50,000 times.
Figure 16:
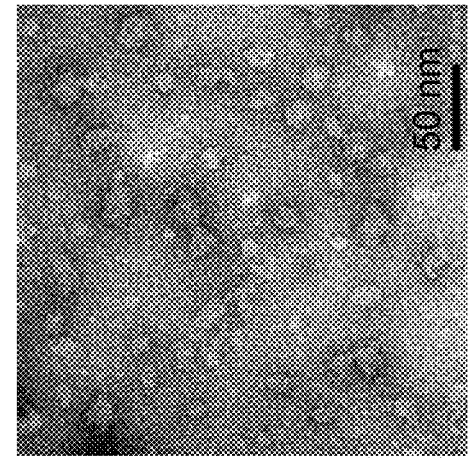
Figure 16:
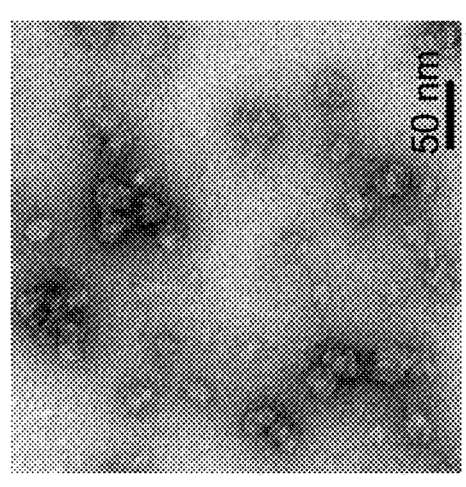

In addition to myoglobin, bovine serum albumin (BSA) and lysozyme were also selected to evaluate the enclosing ability of micelles, because their size (molecular weight) and net charge (isoelectric point) differ from those of myoglobin. As a result, PEG-p(Lys-CDM) was shown to have the ability to enclose these proteins within micelles (Table 3). Further, TEM observation clarified the particle morphology of micelles enclosing these proteins (FIG. 16). These results indicate that the micelle system of the present invention for protein enclosure has a multiplicity of uses.

S4. Enclosure of Different Proteins into Polymeric Micelles

As shown in Table 3, PEG-p(Lys-CDM) was able to form micelles with a narrow particle size distribution when using various proteins with different molecular weights and different isoelectric points (pI).

TABLE 3

Enclosure of proteins into polymeric micelles. The molecular weight and isoelectric point of each protein were obtained from the previously reported documents[S1-S6]. The enclosure efficiency and size distribution of protein-enclosing micelles were determined experimentally.

| | | | Protein-enclosing micelle | | |
|---|---|---|---|---|---|
| Protein | Molecular weight[a] | pI[a] | Enclosure efficiency (%)[b] | Size (nm)[c] | PDI[c] |
| BSA | 66,000 | 4.7 | 56 | 45 | 0.19 |
| Myoglobin | 17,600 | 7 | 62 | 40 | 0.18 |
| Lysozyme | 14,000 | 11.4 | 63 | 48 | 0.23 |
| Antibody (IgG) | 150,000 | ~8.0 | | 70 | 0.11 |
| Antibody fragment (Fab) | 50,000 | ~8.0 | | 50 | 0.12 |
| Cytokine (IL-2, IL-12) | 15,000-75,000 | 5.5-62 | 80 | 45-55 | 0.12-0.14 |

[a]obtained from the documents and the information provided by manufactures.
[b]measured by GPC. The amount of protein enclosed is divided by the total amount of protein supplied.
[c]determined by DLS.

2.5. Preparation of Control Myoglobin-Enclosing Micelles

To evaluate the efficacy of myo/m prepared above, control micelles were constructed to comprise no covalent bond. For preparation of control micelles, the inventors of the present invention first modified myoglobin with CDM by slowly adding CDM to a myoglobin solution. The introduction rate of CDM was 92.8% as measured by the fluorescamine method, and the zeta potential of CC-myo was −29.5 mV, which was reduced from the zeta potential of native myoglobin (−9.2 mV). This indicates that CDM introduction caused charge conversion. Subsequently, in phosphate buffered physiological saline (10 mM phosphate buffer containing 150 mM NaCl, pH 7.4), PEG-p(Lys) was mixed with CC-myo at an N/C (amino group/carboxyl group) ratio of 2:1 to prepare PIC micelles. As a control, a mixture of PEG-p(Lys) and native myoglobin was prepared at the same N/C ratio as above. CC-myo was found to form PIC micelles with PEG-p(Lys) through electrostatic interaction (Table 1). However, myoglobin without CDM modification did not form micelles with PEG-p(Lys). This is probably because the nonuniform surface charge of myoglobin is disadvantageous to stable multi-ion complex[4].

2.6. Stability of Micelles

The stability of micelles was examined by using buffers of different salt concentrations and different pHs.

Figure 5:
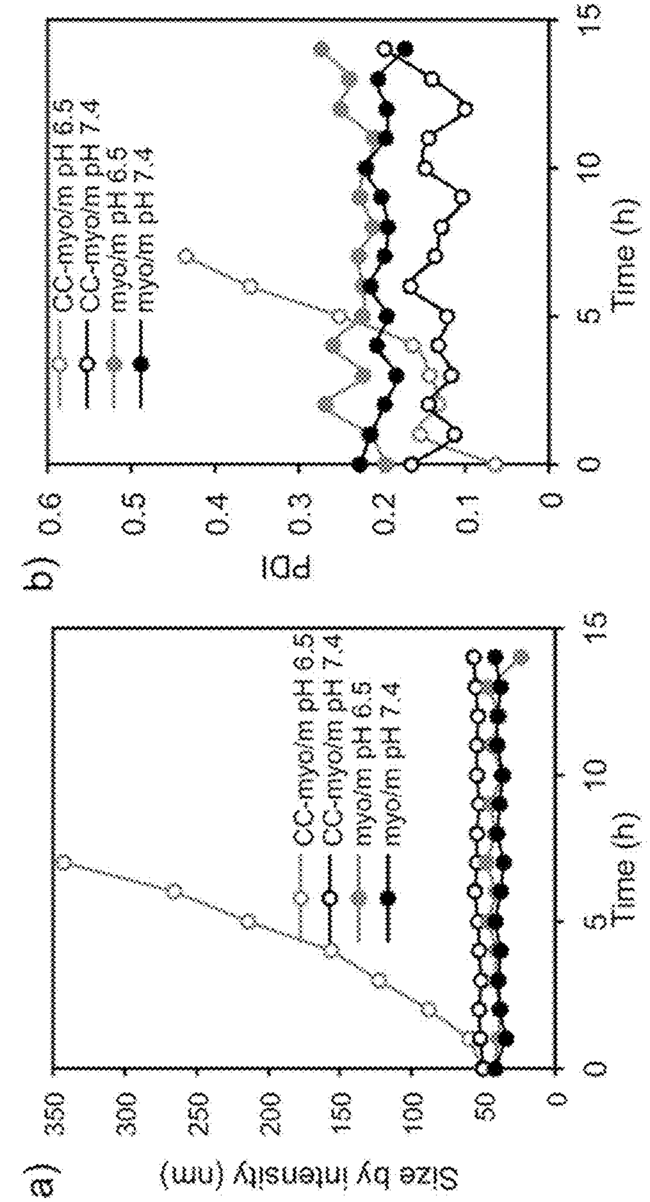
FIG. 5 shows the stability of protein-enclosing micelles in solutions of different pHs. (a) Particle size and (b) PDI of myo/m (gray circles and black circles) and CC-myo/m (white circles) in 10 mM phosphate buffers of pH 6.5 (gray line) and pH 7.4 (black line).

First, a pH stability test was conducted by evaluating the breakdown of micelles consisting of PEG-p(Lys-CDM) (myo/m) and control micelles (CC-myo/m) in 10 mM phosphate buffered physiological saline (pH 6.5 or pH 7.4). The micelles were measured for their size and PDI by DLS every 1 hour. In the case of myo/m, their size and PDI remained unchanged at both pH 7.4 and 6.5, thus indicating that myo/m had high stability. CC-myo/m showed high stability at pH 7.4, as shown in FIG. 5. On the other hand, CC-myo/m rapidly became unstable at pH 6.5. Moreover, myo/m had salt tolerance at both pH 6.5 and pH 7.4 (FIG. 5), whereas empty PIC micelles were quickly broken down under the same conditions (FIG. 3). This suggested that the protein served to stabilize the micelles consisting of PEG-p(Lys-CDM).

Figure 6:
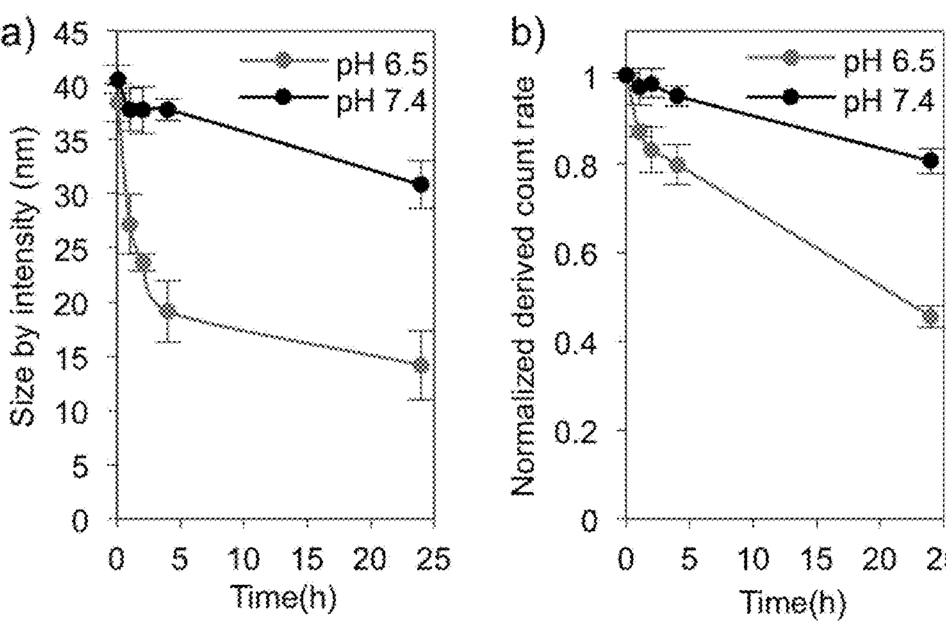
FIG. 6 shows the stability of myo/m diluted with 10 mM phosphate buffers of different pHs containing 600 mM NaCl. (a) Particle size and (b) normalized derived count rate of myo/m in buffers of pH 6.5 (gray line) and pH 7.4 (black line). The data indicate that myo/m were broken down in the buffer of pH 6.5.

PIC micelles are regarded as being difficult to use for biomedical application, because electrostatic interaction holding the micelle structure is dissociated during their retention in blood[25,26]. Thus, in light of the finding that electrostatic interaction[25,27] in micelles is completely inhibited by high NaCl concentration (600 mM), the stability of micelles was evaluated by dialysis in a dialysis cassette with a MWCO of 20,000 against 5 L of 10 mM phosphate buffer of pH 7.4 or 6.5 containing 600 mM NaCl under dilution conditions. Samples were taken over time and analyzed by DLS for monitoring the micelle stability. The control CC-myo/m based solely on PIC was dissociated immediately after being allowed to stand under high salt concentration, whereas myo/m showed rapid reductions in their size and derived count rate after 24 hours at pH 6.5 when compared to pH 7.4. This indicates that the micelles are rapidly broken down at acidic pathological pH, whereas they have strong stability at physiological pH (FIG. 6).

2.7. Myoglobin Release from Myo/m

Figure 7:
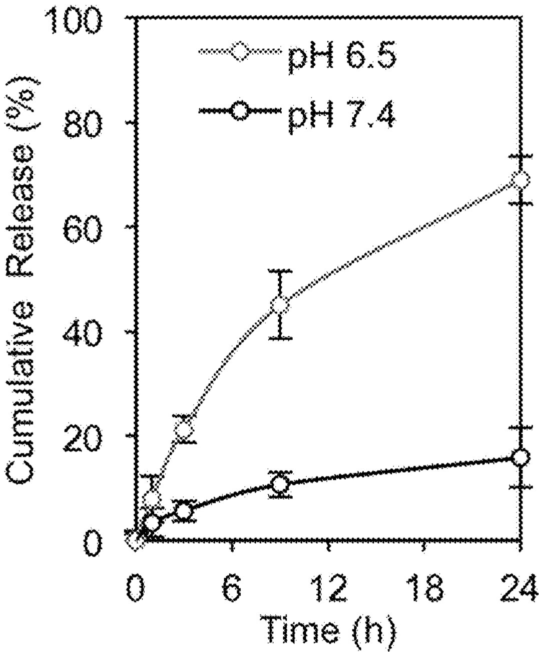
FIG. 7 shows the release of Alexa Fluor 647-labeled myoglobin from myo/m in 10 mM phosphate buffer containing 150 mM NaCl (pH 7.4, pH 6.5).

The release of myo/m from micelles was evaluated by dialyzing Alexa Fluor 647-labeled myo/m-enclosing micelles against 5 L of 10 mM phosphate buffered physiological saline of pH 7.4 or pH 6.5. In this case, the fluorescence intensity of the micelles within a dialysis cassette was measured over time. At pH 7.4, myo/m slowly released the protein enclosed therein (FIG. 7). On the other hand, myoglobin release from the micelles was accelerated at pH 6.5, and about 70% of the enclosed protein was released within 24 hours (FIG. 7). These results are correlated with micelle stability at pH 7.4 and rapid breakdown at pH 6.5, and strongly suggest that the micelles respond to pathological pH and ionic strength (150 mM NaCl).

2.8. Myoglobin Activity

Myoglobin oxidation can be determined by shifts of the Soret band (380 to 460 nm) and the Q band (480 to 650 nm)[22,28-30]. Thus, the activity of myoglobin released from myo/m at pH 6.5 was evaluated by UV/Vis spectroscopy. When sodium dithionite was added to the released myoglobin solution, the Soret band appeared at 434 nm. This corresponds to the band of deoxymyoglobin. Further, a blue shift of the Soret band from 434 nm to 414 nm, and a peak split of the Q band were observed after $O_2$ introduction. This corresponds to the band of oxymyoglobin[22,28,29].

Figure 8:
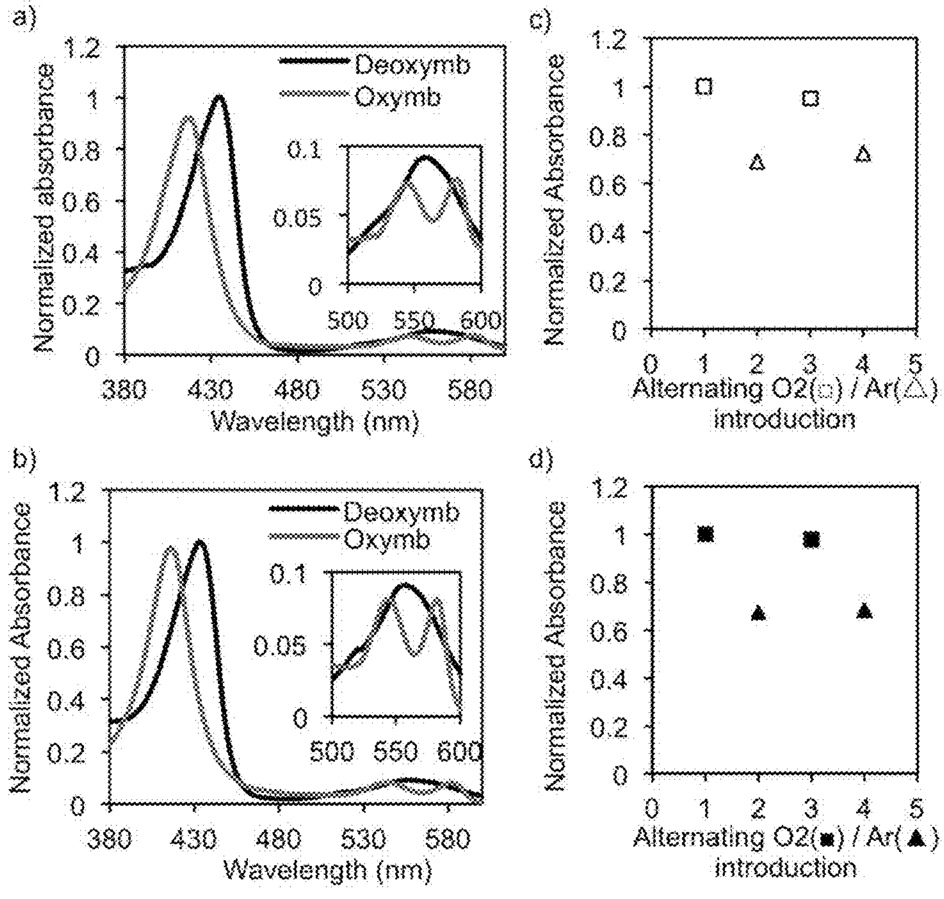
FIG. 8 shows the evaluation of myoglobin activity. a) UV/Vis absorption spectrum of oxymyoglobin after introduction of $O_2$ gas (gray line) and deoxymyoglobin after introduction of Ar gas (black line). The inset is the spectrum obtained at 500 to 600 nm for myoglobin released from micelles. b) UV/Vis absorption spectrum of native oxymyoglobin after introduction of $O_2$ gas (gray line) and deoxymyoglobin after introduction of Ar gas (black line). The inset is the spectrum obtained at 500 to 600 nm for native myoglobin. c-d) Absorbances at 414 nm of released myoglobin (c, white marks) and native myoglobin (d, black marks) upon alternate introduction of $O_2$ (square marks)/Ar (triangle marks) gas.

When the released myoglobin solution was then bubbled with Ar gas, inverse changes occurred in the Soret band and the Q band, thus confirming deoxidation (FIG. 8*a*). Moreover, released myoglobin successfully underwent a conformational change between oxymyoglobin and deoxymyoglobin upon alternate bubbling with $O_2$ or argon gas (FIG. 8*c*). As a control, native myoglobin was used (FIG. 8*b, d*). Further, there was no significant difference in oxidation or deoxidation between native myoglobin and myoglobin released from myo/m. These results indicate that the protein enclosed within myo/m remains functional at the time of release.

2.9. In Vivo Blood Retention and In Vivo Distribution

Most therapeutic proteins have reduced blood retention due to their aggregation in blood and their rapid renal excretion[31,32]. In this example, to test PEG-p(Lys-CDM)-based micelles for their performance to improve protein pharmacokinetics, myoglobin was used as a model protein, which has been known to aggregate in blood and undergo renal excretion[34]. Myoglobin was fluorescently labeled with Alexa Fluor 647, enclosed within the micelles and examined for in vivo blood retention and in vivo distribution.

Figure 9:
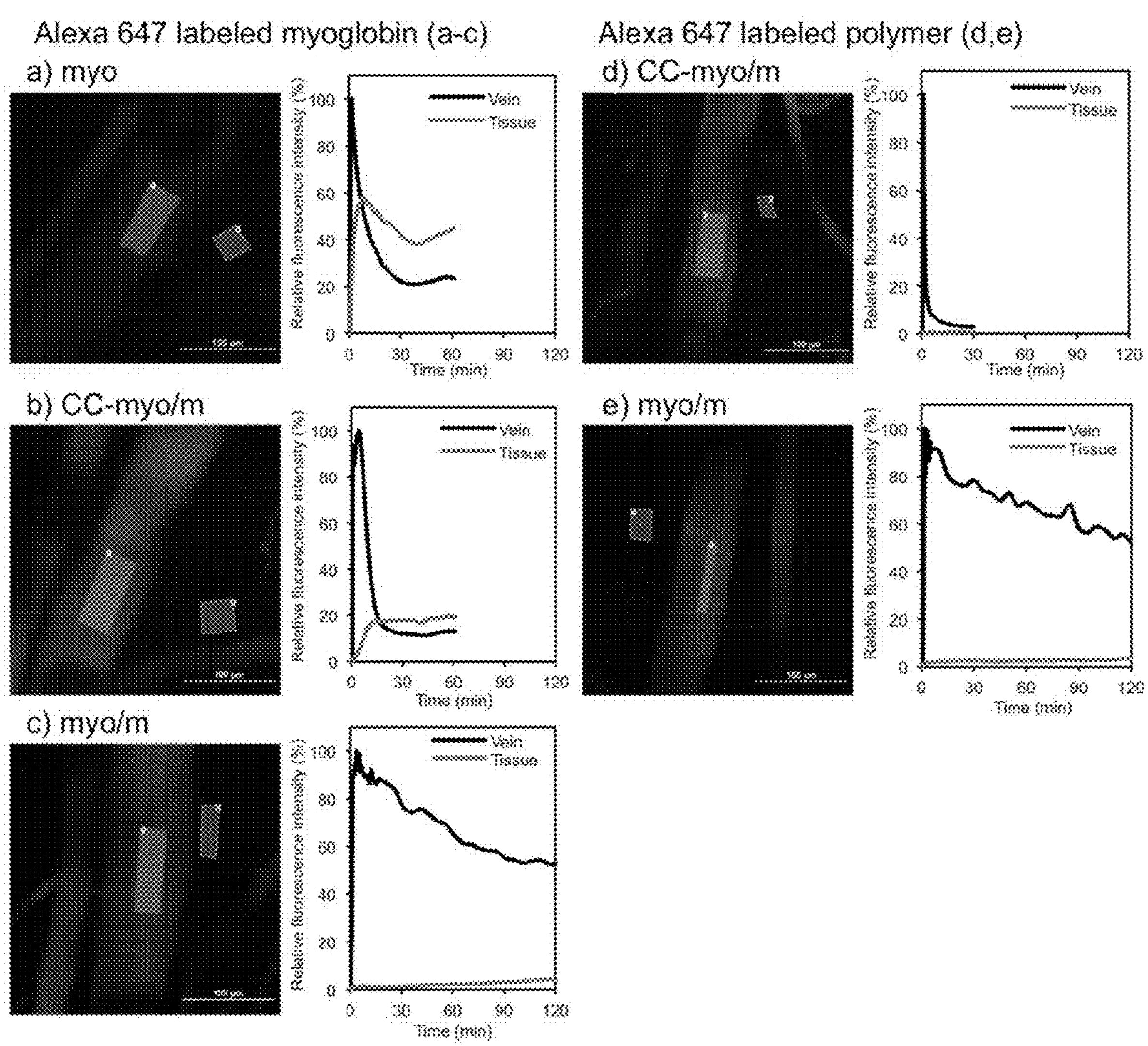
FIG. 9 shows the blood retention of fluorescently labeled myoglobin, CC-myo/m and myo/m, as measured by IV-CLSM. a)-c): a) myoglobin alone, b) CC-myo/m and c) myo/m, each being prepared with Alexa Fluor 647-labeled myoglobin (red). d)-e): d) CC-myo/m and e) myo/m, each being prepared with Alexa Fluor 647-labeled polymer (red). Fluorescence intensities in vein (red trapezoid) and skin (green trapezoid) in microscopic images (left panels in a to e) obtained immediately after sample administration were used for normalization and quantification (right panels in a to e).

Fluorescently labeled myo/m showed a size distribution similar to that of non-labeled micelles. After intravenous injection, the blood retention of the fluorescently labeled micelles was recorded by real-time IV-CLSM. As shown in FIG. 9*a* to *c*, covalently stabilized myo/m showed a half-life exceeding 120 minutes, whereas CC-myo/m (10 minutes) and free myoglobin (9 minutes) showed short half-lives. Further, CC-myo/m and free myoglobin showed strong fluorescence signals in the skin parenchymal tissue, whereas myo/m did not emigrate to the skin. This indicates that the enclosed myoglobin is not leaked out from the micelles in blood.

Then, myo/m and CC-myo/m prepared from Alexa Fluor 647-labeled polymer and non-labeled myoglobin were used to evaluate in vivo blood retention and in vivo distribution of the polymer. myo/m showed a half-life of 120 minutes or longer, as in the case where myoglobin was labeled, whereas CC-myo/m showed a half-life of only 1 minute and were not detected in blood after 5 minutes. Since PEG-p(Lys) is rapidly excreted from blood within a few minutes, CC-myo/m is considered to be unstable in blood. This is in correspondence with the finding that the half-life of fluorescently labeled myoglobin in CC-myo is equal to the half-life of myoglobin alone (FIG. 9*a, b*), thus indicating that charge-converted myoglobin micelles are rapidly broken down in blood. On the other hand, myo/m showed high stability in blood (FIG. 9*c, e*). This is because the blood retention of fluorescently labeled polymer PEG-p(Lys-CDM) is in correspondence with the blood retention of the fluorescently labeled protein.

Myoglobin, CC-myo/m and myo/m were evaluated for in vivo distribution in main organs involved in the excretion of nanoparticles (i.e., kidney, liver and spleen) at 12 hours after administration.

Figure 10:
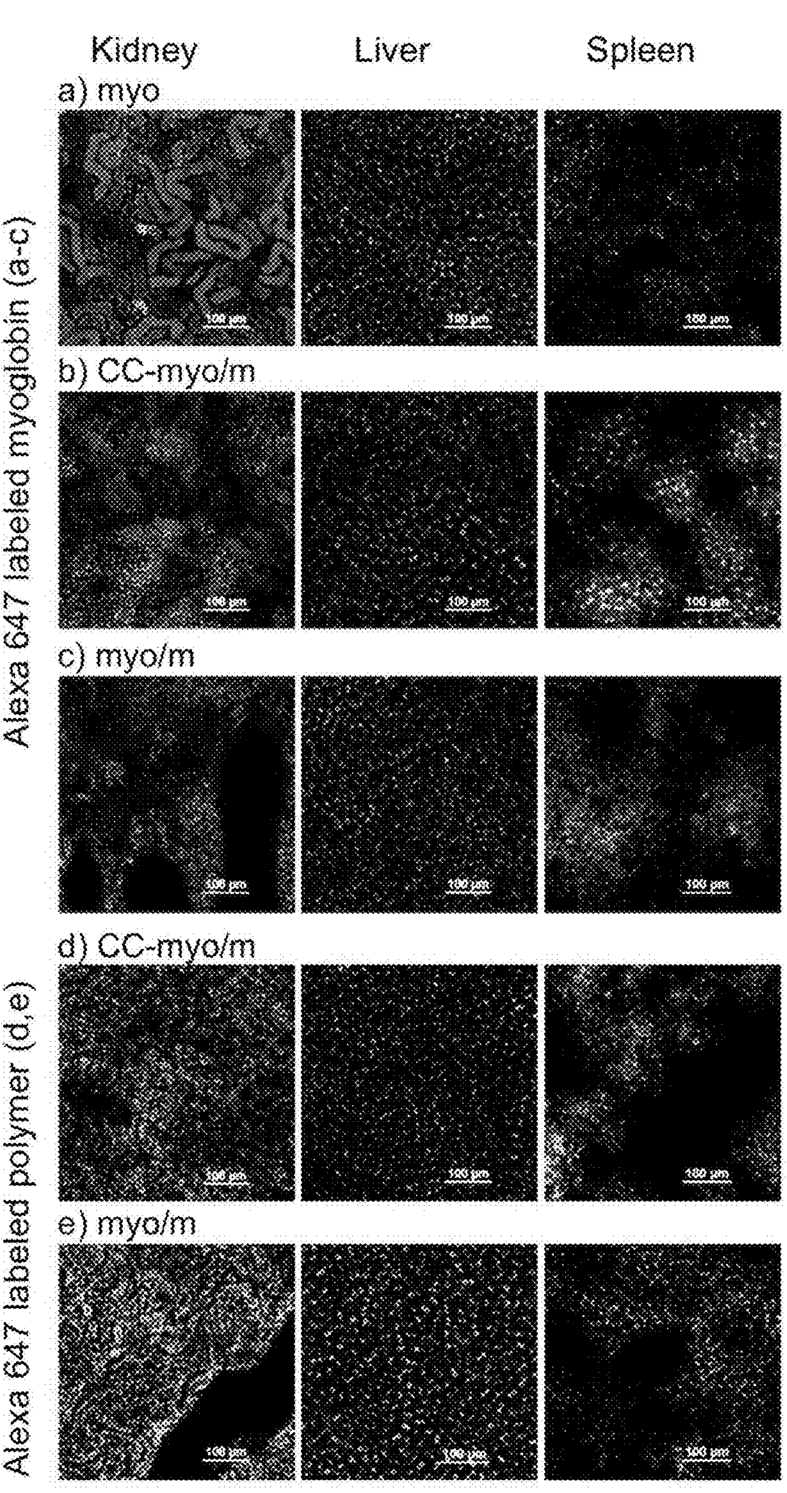
FIG. 10 shows the microdistribution of fluorescently labeled myoglobin, CC-myo/m and myo/m in the kidney, liver and spleen. a)-c): a) myoglobin alone, b) CC-myo/m and c) myo/m, each being prepared with Alexa Fluor 647-labeled myoglobin (red). d)-e): d) CC-myo/m and e) myo/m, each being prepared with Alexa Fluor 647-labeled polymer (red). Cell nuclei were stained with Hoechst (cyan). Scale bar: 100 μm.

Cell nuclei were stained by tail vein administration of Hoechst at 30 minutes before imaging. Then, the kidney, liver and spleen were taken out and observed by ex vivo fluorescence imaging. As shown in FIG. 10*a* to *c*, free myoglobin and CC-myoglobin showed high accumulation in the kidney, which is in agreement with the rapid excretion of free myoglobin and CC-myo/m from blood. On the other hand, the myo/m micelles were prevented from accumulation in the kidney when compared to CC-myo/m and myoglobin, and were accumulated in the liver.

Further, in the case of CC-myo/m monitored using Alexa Fluor 647-labeled PEG-p(Lys), almost no fluorescence signals were detected in the kidney, liver and spleen due to the rapid excretion of the polymer (FIG. 10*d*). On the other hand, signals from myo/m monitored using Alexa Fluor 647-labeled PEG-p(Lys-CDM) were observed mainly in the liver (FIG. 10*e*), which is in agreement with the distribution of myo/m enclosing fluorescently labeled myoglobin (FIG. 10*c*). These results demonstrate the high stability of myo/m in blood, and indicate that PEG-p(Lys-CDM) is useful for the preparation of protein-enclosing micelles intended for in vivo delivery.

3. Conclusion

The inventors of the present invention have succeeded in developing pH-responsive polymeric micelles for protein enclosure by using a novel polymer, PEG-p(Lys-CDM), which can enclose a protein by means of combination of polyion complex formation and pH-responsive amide bonding. By using myo/m as a model, the inventors of the present invention have demonstrated that these micelles are stable at pH 7.4, but are rapidly broken down at pH 6.5. Further, the myoglobin-enclosing micelles of the present invention showed high blood retention in vivo, when compared to free myoglobin and micelles self-assembled alone by PIC formation. Further, myoglobin released from the micelles at pH 6.5 was shown to have the same oxidation and reduction ability as native myoglobin, thus indicating that the micelles of the present invention can maintain the function of the protein enclosed therein. These findings indicate the potential of the micelles of the present invention as a protein nanocarrier which targets pathological tissues and is effective in the in vivo spatial-temporal regulation of protein activity.

References

[1] R. Langer, D. A. Tirrell, Nature 2004, 428, 487-492.
[2] B. Romberg, W. E. Hennink, G. Storm, Pharm. Res. 2008, 25, 55-71.
[3] V. Torchilin, Adv. Drug Deliv. Rev. 2011, 63, 131-135.
[4] H. Cabral, K. Miyata, K. Osada, K. Kataoka, Chem. Rev. 2018, 118, 6844-6892.
[5] Y. Qi, A. Chilkoti, Curr. Opin. Chem. Biol. 2015, 28, 181-193.
[6] S. N. S. Alconcel, A. S. Baas, H. D. Maynard, Polym. Chem. 2011, 2, 1442-1448.
[7] F. M. Veronese, G. Pasut, Drug Discov. Today 2005, 10, 1451-1458.
[8] F. F. Abuchowski, A., McCoy, J. R., Palczuk, N. C., van Es, T., Davis, J. Biol. Chem. 1977, 252, 3582-3586.
[9] J. L. Kaar, K. Matyjaszewski, A. J. Russell, C. M. Colina, A. Simakova, B. S. Sumerlin, C. A. Figg, S. L. Baker, AIChE J. 2018, 64, 3230-3245.
[10] Y. Lu, W. Sun, Z. Gu, J. Control. Release 2014, 194, 1-19.
[11] S. Mura, J. Nicolas, P. Couvreur, Nat. Mater. 2013, 12, 991.
[12] L. E. Gerweck, K. Seetharaman, Cancer Res. 1996, 56, 1194 LP-1198.
[13] G. Helmlinger, F. Yuan, M. Dellian, R. K. Jain, Nat. Med. 1997, 3, 177-182.
[14] Y. Lee, T. Ishii, H. Cabral, H. J. Kim, J. H. Seo, N. Nishiyama, H. Oshima, K. Osada, K. Kataoka, Angew. Chemie—Int. Ed. 2009, 48, 5309-5312.
[15] Y. Lee, T. Ishii, H. J. Kim, N. Nishiyama, Y. Hayakawa, K. Itaka, K. Kataoka, Angew. Chemie 2010, 122, 2606-2609.
[16] A. Kim, Y. Miura, T. Ishii, O. F. Mutaf, N. Nishiyama, H. Cabral, K. Kataoka, Biomacromolecules 2016, 17, 446-453.
[17] P. J. G. Butler, J. I. Harris, B. S. Hartley, R. Leberman, Biochem. J. 1969, 112, 679-689.
[18] K. Maier, E. Wagner, J. Am. Chem. Soc. 2012, 134, 10169-10173.
[19] Y. Liu, J. Du, C. Sun, C. Xu, Z. Cao, J. Wang, Angew. Chemie Int. Ed. 2015, 55, 1010-1014.
[20] H. C. Yen, H. Cabral, P. Mi, K. Toh, Y. Matsumoto, X. Liu, H. Koori, A. Kim, K. Miyazaki, Y. Miura, et al., ACS Nano 2014, 8, 11591-11602.
[21] D. B. Rozema, D. L. Lewis, D. H. Wakefield, S. C. Wong, J. J. Klein, P. L. Roesch, S. L. Bertin, T. W. Reppen, Q. Chu, A. V. Blokhin, et al., Proc. Natl. Acad. Sci. 2007, 104, 12982-12987.
[22] A. Kishimura, A. Koide, K. Osada, Y. Yamasaki, K. Kataoka, Angew. Chemie—Int. Ed. 2007, 46, 6085-6088.
[23] K. Matsumoto, Y.; Nomoto, T.; Cabral, H.; Matsumoto, Y.; Watanabe, S.; Christie, R. J.; Miyata, K.; Oba, M.; Ogura, T.; Yamasaki, Y.; Nishiyama, N.; Yamasoba, T.; Kataoka, Biomed. Opt. Express 2010, 1, 1209.
[24] F. Chen, R. Raveendran, C. Cao, R. Chapman, M. H. Stenzel, Polym. Chem. 2019, 10, 1221-1230.
[25] H. Takemoto, A. Ishii, K. Miyata, M. Nakanishi, M. Oba, T. Ishii, Y. Yamasaki, N. Nishiyama, K. Kataoka, Biomaterials 2010, 31, 8097-8105.
[26] M. Harada-Shiba, K. Yamauchi, A. Harada, I. Takamisawa, K. Shimokado, K. Kataoka, Gene Ther. 2002, 9, 407.
[27] Y. Wang, K. Kimura, Q. Huang, P. L. Dubin, W. Jaeger, Macromolecules 1999, 32, 7128-7134.
[28] Q. C. Li, P. A. Mabrouk, J. Biol. Inorg. Chem. 2003, 8, 83-94.
[29] M. C. Hsu, R. W. Woody, J. Am. Chem. Soc. 1971, 93, 3515-3525.
[30] R. M. Esquerra, R. A. Goldbeck, D. B. Kim-Shapiro, D. S. Kliger, Biochemistry 1998, 37, 17527-17536.
[31] F. M. Veronese, A. Mero, BioDrugs 2008, 22, 315-329.
[32] T. Arvinte, C. Palais, E. Green-Trexler, S. Gregory, H. Mach, C. Narasimhan, M. Shameem, in MAbs, Taylor & Francis, 2013, pp. 491-500.
[33] L. J. Kagen, A. Butt, Clin. Chem. 1977, 23, 1813-1818.
[34] R. Vanholder, M. S. Sever, E. Erek, N. Lameire, J. Am. Soc. Nephrol. 2000, 11, 1553-1561.

Supplementary References

[S1] L. R. Wetter, H. F. Deutsch, J. Biol. Chem. 1951, 192, 237-42.
[S2] R. E. Canfield, J. Biol. Chem. 1963, 238, 2698-2707.

[S3] Q. Shi, Y. Zhou, Y. Sun, Biotechnol. Prog. 2005, 21, 516-523.
[S4] K. Hirayama, S. Akashi, M. Furuya, K. Fukuhara, Biochem. Biophys. Res. Commun.
1990, 173, 639-646.
[S5] B. J. Radola, Biochim. Biophys. Acta—Protein Struct. 1973, 295, 412-428.
[S6] P. D. Darbre, A. E. Romero-Herrera, H. Lehmann, Biochim. Biophys. Acta—Protein Struct. 1975, 393, 201-204.

Example 2

1. Preparation of IL-12-Enclosing Micelles

In this example, IL-12-enclosing micelles were prepared by precise control of pH. In brief, 2.5 mg of PEG-P(Lys-CDM) was dissolved in 0.5 mL of 20 mM phosphate buffer (pH 5), and then allowed to stand for 1 hour in order that the polymer was prevented from autonomously associating to form empty micelles. 10 μg of IL-12 was dissolved in 0.5 mL of 20 mM phosphate buffer (pH 8). The IL-12 solution was added at a rate of 5 μL/minute to the polymer solution under stirring (shaking) conditions, followed by continuous stirring (shaking) for 6 hours. Then, 1 mL of the buffer (pH 8) was added to the mixture, and the mixed solution was stirred (shaken) overnight.

The enclosure efficiency was measured by ELISA assay. The concentration of free IL-12 not enclosed in the mixture was detected with an ELISA kit to calculate the amount of IL-12 enclosed.

As a result, the concentration of free IL-12 in 2 mL of the mixed solution was 1.6 μg/mL. The total concentration of IL-12 was 5 μg/mL, and hence the enclosure efficiency was calculated to be 68%.

2. Purification and Characterization of IL-12-Enclosing Micelles

Purification was accomplished by the dialysis method. The mixed solution was charged into a dialysis cassette with a MWCO of 100 kDa, and then dialyzed overnight at 4° C. against 10 mM phosphate buffer (pH 7.4) and 150 mM NaCl. Then, the purified micelle solution was subjected to precision concentration adjustment (adjusted to have a polymer concentration of 1 mg/mL) for size and zeta potential measurement with a Zetasizer.

Figure 17:
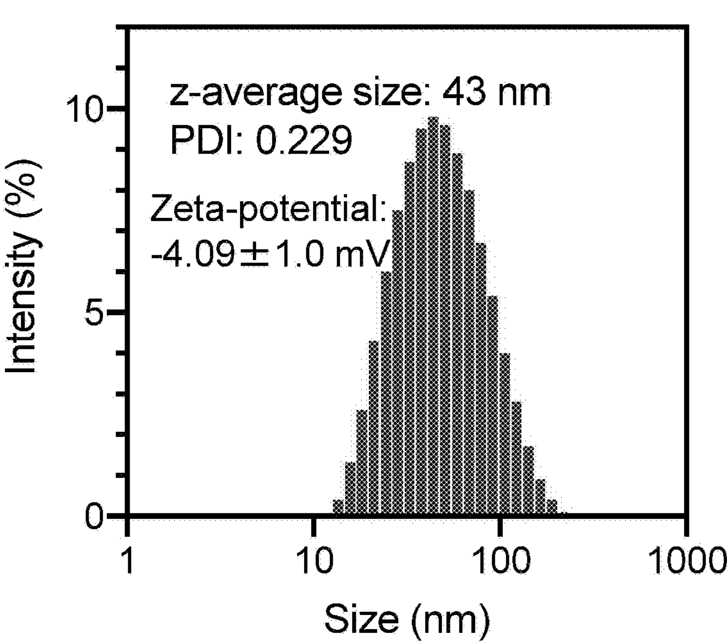
FIG. 17 shows the micelle size distribution of IL-12-enclosing micelles.

As a result, the z-average size was 43 nm and PDI was 0.229, as measured by DLS (FIG. 17). The surface of the micelles was slightly negatively charged, and the zeta potential was −4.1±1.0 mV.

3. In Vitro Drug Release Experiment

In this section, the dialysis method was used again. The purified micelle solution was charged into a dialysis cassette with a MWCO of 100 kDa, and then dialyzed at room temperature against 500 mL of 10 mM phosphate buffer (pH 7.4)+150 mM NaCl or against 500 mL of 10 mM phosphate buffer (pH 6.5)+150 mM NaCl. At given time points, the solution was sampled from the outside of the cassette, and the concentration of IL-12 in each sample was determined by ELISA assay.

Figure 18:
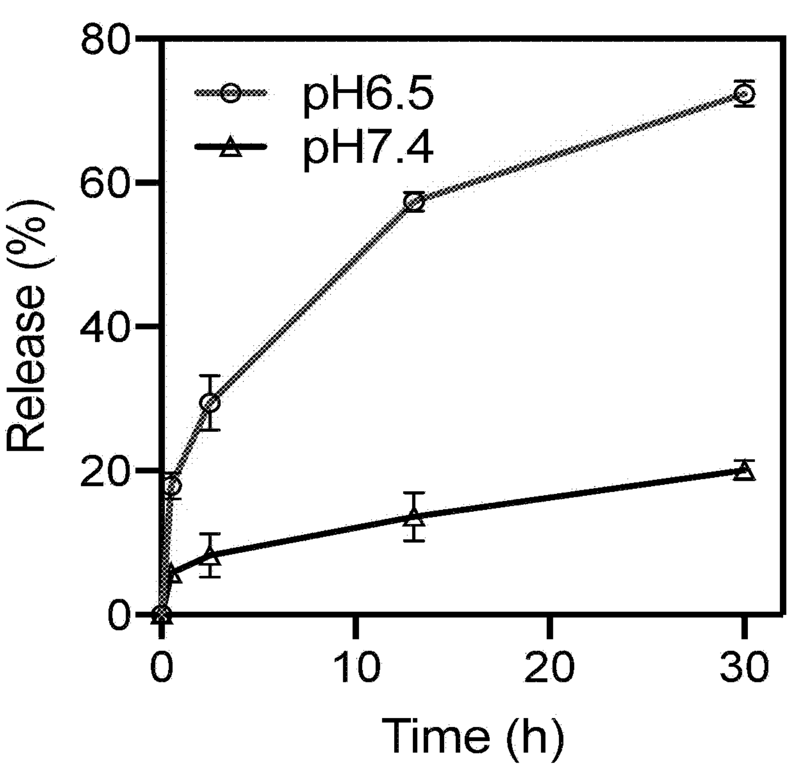
FIG. 18 shows IL-12 release from IL-12-enclosing micelles.

As a result, the micelles were found to be pH-responsive. After 30 hours, the amount of IL-12 released at pH 6.5 was about 4 times greater than the amount of IL-12 released at pH 7.4 (FIG. 18).

4. In Vitro Cell Experiment

In this section, the amount of INF-γ secretion from mouse spleen cells was measured to evaluate the physiological activity of the micelles and IL-12 released therefrom.

BALB mice at 9 weeks of age were sacrificed to collect spleen cells from their spleens. Then, the collected spleen cells were seeded in 96-well plates at a concentration of $1\times10^5$ cells per well. The micelle solution was dialyzed against a buffer (pH 5). For concentration adjustment, the outside solution was then ultracentrifuged to isolate IL-12 released from the micelles. The micelles and the released IL-12 were each added at different concentrations to wells, and native IL-12 was used as a standard. After the plates were allowed to stand for 24 hours or 48 hours, the supernatant in each well was removed and measured for INF-γ concentration with an ELISA kit.

Figure 19:
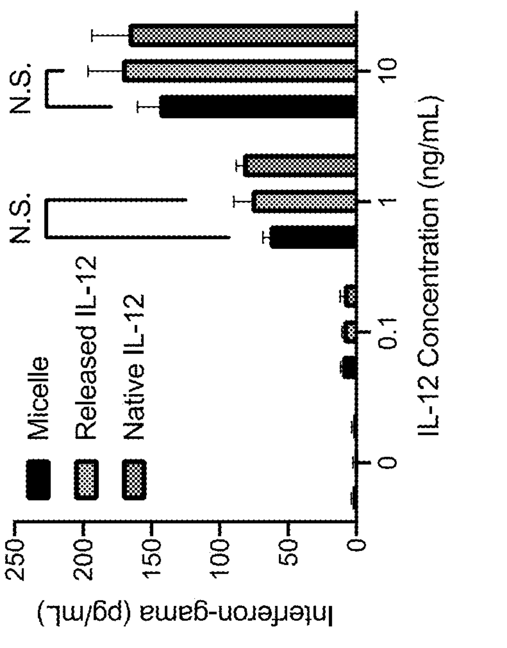
FIG. 19 shows the amount of INF-γ secretion induced by IL-12-enclosing micelles in mouse spleen cells.

As a result, after 24 hours, the IL-12-enclosing micelles more significantly suppressed the elevation of INF-γ concentration than the released IL-12, thus indicating that micellization suppressed the binding of IL-12 to its receptor (FIG. 19). The difference between the released IL-12 and native IL-12 is not statistically significant, thus indicating that micellization does not affect the physiological activity of the enclosed protein. After 48 hours, the differences among the three groups were reduced. This phenomenon is due to the breakdown of the micelles.

The invention claimed is:

1. A polymeric complex comprising a protein and a block copolymer represented by the following formula (1):

(1)

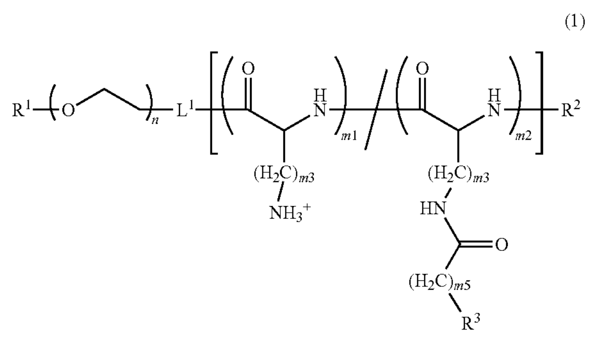

wherein $R^1$ represents an optionally substituted linear or branched alkyl group containing 1 to 12 carbon atoms and $R^2$ represents a hydrogen atom, $R^3$ represents a compound represented by the following formula (Ia) or (Ib), (Ia)

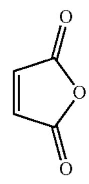

(Ib)

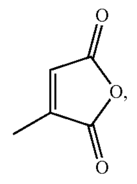

$L^1$ represents NH or a group represented by the following formula (11):

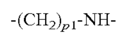

$-(CH_2)_{p1}-NH-$ (11), wherein p1 represents an integer of 1 to 6, m1 and m2 each represent an integer of 0 to 500, provided that the sum of m1 and m2 represents an integer of 10 to 500, and with the proviso that m1 is not 0 and m2 is not 0, m3, m4 and m5 each independently represent an integer of 1 to 5, and n represents an integer of 1 to 500, and the symbol "/" means that (m1+m2) units of the respective monomer units shown on the left and right sides of this symbol may be in any sequence.

2. The complex according to claim 1, wherein the block copolymer represented by formula 1 is a block copolymer represented by the following formula (2), (2)

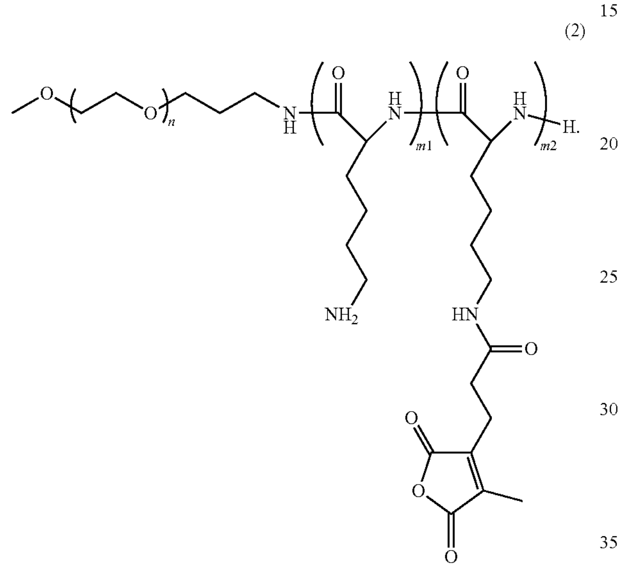

3. The complex according to claim 1, wherein the protein is covalently bonded to the block copolymer represented by formula 1.

4. The complex according to claim 3, wherein the covalent bond is cleaved in a pH-dependent manner.

5. A protein delivery device comprising the polymeric complex according to claim 1 for use in protein delivery to any site selected from a cell surface site, an intracellular site and an extracellular site.

6. A protein delivery kit comprising a block copolymer represented by the following formula (1) for use in protein delivery to any site selected from a cell surface site, an intracellular site and an extracellular site:

(1)

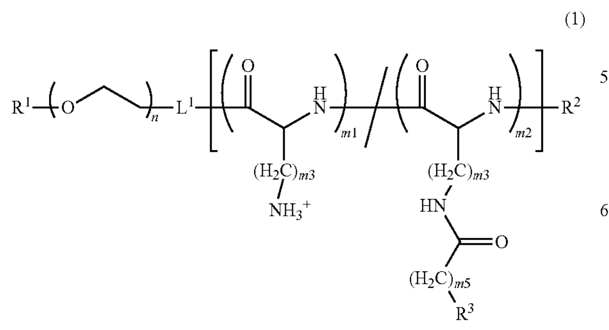

wherein $R^1$ represents an optionally substituted linear or branched alkyl group containing 1 to 12 carbon atoms and $R^2$ represents a hydrogen atom, $R^3$ represents a compound represented by the following formula (Ia) or (Ib), (Ia)

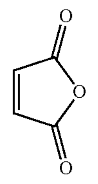

(Ib)

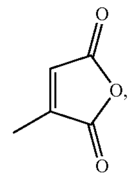

$L^1$ represents NH or a group represented by the following formula (11):

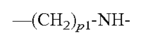

$$-(CH_2)_{p1}-NH- \quad (11)$$

wherein p1 represents an integer of 1 to 6, m1 and m2 each independently represent an integer of 0 to 500 provided that the sum of m1 and m2 represents an integer of 1 to 500 and with the proviso that m1 is not 0 and m2 is not 0, m3, m4 and m5 each independently represent an integer of 1 to 5, and n represents an integer of 1 to 500, and the symbol "/" means that (m1+m2) units of the respective monomer units shown on the left and right sides of this symbol may be in any sequence.

7. The kit according to claim 6, wherein the block copolymer represented by formula 1 is a block copolymer represented by the following formula (2), (2)

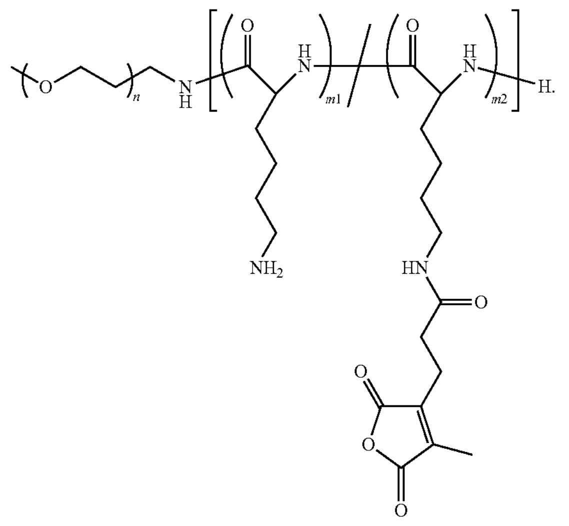

* * * * *